US007087075B2

(12) United States Patent
Briscoe et al.

(10) Patent No.: US 7,087,075 B2
(45) Date of Patent: Aug. 8, 2006

(54) FEEDBACK SYSTEM FOR RAPID INDUCTION OF MILD HYPOTHERMIA

(75) Inventors: Kathleen E. Briscoe, Carnation, WA (US); Stephen W. Radons, Snohomish, WA (US); Larry R. Nygaard, Snohomish, WA (US); Joseph L. Sullivan, Kirkland, WA (US)

(73) Assignee: Medtronic Emergency Response Systems, Inc., Redmond, WA (US)

( * ) Notice: Subject to any disclaimer, the term of this patent is extended or adjusted under 35 U.S.C. 154(b) by 192 days.

(21) Appl. No.: 10/262,680

(22) Filed: Sep. 30, 2002

(65) Prior Publication Data

US 2004/0064171 A1    Apr. 1, 2004

(51) Int. Cl.
*A61F 7/00* (2006.01)
(52) U.S. Cl. ............... 607/104; 607/108; 607/109; 607/110
(58) Field of Classification Search .......... 607/104, 607/107–114; 606/22, 25
See application file for complete search history.

(56) References Cited

U.S. PATENT DOCUMENTS

| 3,504,674 | A |   | 4/1970  | Swenson et al. |
|-----------|---|---|---------|----------------|
| 3,587,577 | A |   | 6/1971  | Smirnov et al. |
| 3,648,765 | A | * | 3/1972  | Starr ............... 165/300 |
| 3,811,777 | A |   | 5/1974  | Chance |
| 3,830,222 | A |   | 8/1974  | Chance |
| 3,871,381 | A |   | 3/1975  | Roslonski |
| 3,963,351 | A |   | 6/1976  | Chance et al. |
| 4,023,905 | A |   | 5/1977  | Chance |
| 4,118,946 | A |   | 10/1978 | Tubin |
| 4,138,743 | A |   | 2/1979  | Elkins et al. |
| 4,162,405 | A |   | 7/1979  | Chance et al. |
| 4,172,495 | A |   | 10/1979 | Zebuhr et al. |
| 4,191,028 | A | * | 3/1980  | Audet et al. ............... 62/259.1 |
| 4,292,973 | A |   | 10/1981 | Yamauchi et al. |
| 4,353,359 | A |   | 10/1982 | Milbauer |
| 4,378,797 | A |   | 4/1983  | Osterholm |
| 4,380,240 | A |   | 4/1983  | Jobsis et al. |
| 4,382,446 | A |   | 5/1983  | Truelock et al. |
| 4,416,285 | A |   | 11/1983 | Shaw et al. |
| 4,425,916 | A |   | 1/1984  | Bowen |
| 4,441,502 | A |   | 4/1984  | Chance |
| 4,452,250 | A |   | 6/1984  | Chance et al. |
| 4,510,938 | A |   | 4/1985  | Jobsis et al. |

(Continued)

FOREIGN PATENT DOCUMENTS

DE    28 51 602    6/1980

(Continued)

OTHER PUBLICATIONS

The International Preliminary Examination Report for PCT/US03/30695 mailed Dec. 28, 2004 (9 pages).

(Continued)

*Primary Examiner*—Linda C. M. Dvorak
*Assistant Examiner*—Kenneth C. Williams
(74) *Attorney, Agent, or Firm*—Shumaker & Sieffert, P.A.

(57) ABSTRACT

In general, the disclosure presents techniques for control of a cooling garment in response to a signal that is a function of a patient parameter such as body temperature. In particular, a cooling garment that receives a coolant and a carrier gas is placed in contact with the body of a patient. A sensor within the cooling garment may generate a signal as a function of a patient parameter. A controller receives the signal via communication link, and may send a signal to a regulator that may regulate delivery of the coolant and/or carrier gas, for example.

40 Claims, 14 Drawing Sheets

U.S. PATENT DOCUMENTS

| | | |
|---|---|---|
| 4,552,149 A | 11/1985 | Tatsuki |
| 4,570,638 A | 2/1986 | Stoddart et al. |
| 4,638,436 A | 1/1987 | Badger et al. |
| 4,725,147 A | 2/1988 | Stoddart |
| 4,750,493 A | 6/1988 | Brader |
| 4,753,242 A | 6/1988 | Saggers |
| 4,765,338 A | 8/1988 | Turner et al. |
| 4,768,516 A | 9/1988 | Stoddart et al. |
| 4,817,621 A | 4/1989 | Aaslid |
| 4,817,623 A | 4/1989 | Stoddart et al. |
| 4,865,038 A | 9/1989 | Rich et al. |
| 4,869,250 A | 9/1989 | Bitterly |
| 4,904,237 A | 2/1990 | Janese |
| 4,920,963 A | 5/1990 | Brader |
| 4,964,408 A | 10/1990 | Hink et al. |
| 4,972,331 A | 11/1990 | Chance |
| 4,981,136 A | 1/1991 | Chance |
| 4,987,896 A | 1/1991 | Nakamatsu |
| 5,062,428 A | 11/1991 | Chance |
| 5,080,098 A | 1/1992 | Willett et al. |
| 5,081,991 A | 1/1992 | Chance |
| 5,090,415 A | 2/1992 | Yamashita et al. |
| 5,094,240 A | 3/1992 | Muz |
| 5,110,721 A | 5/1992 | Anaise et al. |
| 5,119,815 A | 6/1992 | Chance |
| 5,122,974 A | 6/1992 | Chance |
| 5,139,025 A | 8/1992 | Lewis et al. |
| 5,140,989 A | 8/1992 | Lewis et al. |
| 5,149,321 A | 9/1992 | Klatz et al. |
| 5,163,425 A | 11/1992 | Nambu et al. |
| 5,167,230 A | 12/1992 | Chance |
| 5,187,672 A | 2/1993 | Chance et al. |
| 5,188,108 A | 2/1993 | Secker |
| 5,217,013 A | 6/1993 | Lewis et al. |
| 5,234,405 A | 8/1993 | Klatz et al. |
| 5,261,243 A | 11/1993 | Dunsmore |
| 5,261,399 A | 11/1993 | Klatz et al. |
| 5,269,758 A | 12/1993 | Taheri |
| 5,285,781 A | 2/1994 | Brodard |
| 5,287,705 A | 2/1994 | Roehrich et al. |
| 5,349,961 A | 9/1994 | Stoddart et al. |
| 5,350,417 A | 9/1994 | Augustine |
| 5,353,799 A | 10/1994 | Chance |
| 5,365,607 A | 11/1994 | Benevento, Jr. et al. |
| 5,383,918 A | 1/1995 | Panetta |
| 5,386,827 A | 2/1995 | Chance et al. |
| 5,395,314 A | 3/1995 | Klatz et al. |
| 5,402,778 A | 4/1995 | Chance |
| 5,408,093 A | 4/1995 | Ito et al. |
| 5,409,005 A | 4/1995 | Bissonnette et al. |
| 5,449,379 A | 9/1995 | Hadtke |
| 5,465,714 A | 11/1995 | Scheuing |
| 5,477,853 A | 12/1995 | Farkas et al. |
| 5,482,034 A | 1/1996 | Lewis et al. |
| 5,486,204 A | 1/1996 | Clifton |
| 5,531,776 A | 7/1996 | Ward et al. |
| 5,553,614 A | 9/1996 | Chance |
| 5,555,885 A | 9/1996 | Chance |
| 5,564,417 A | 10/1996 | Chance |
| 5,571,142 A | 11/1996 | Brown et al. |
| 5,584,296 A | 12/1996 | Cui et al. |
| 5,584,804 A | 12/1996 | Klatz et al. |
| 5,596,987 A | 1/1997 | Chance |
| 5,603,728 A | 2/1997 | Pachys |
| 5,658,324 A | 8/1997 | Bailey, Sr. et al. |
| 5,662,690 A | 9/1997 | Cole et al. |
| 5,664,574 A | 9/1997 | Chance |
| 5,673,701 A | 10/1997 | Chance |
| 5,683,438 A | 11/1997 | Grahn |
| 5,697,367 A | 12/1997 | Lewis et al. |
| 5,700,828 A | 12/1997 | Federowicz et al. |
| 5,713,941 A | 2/1998 | Robins et al. |
| 5,716,386 A | 2/1998 | Ward et al. |
| 5,730,730 A | 3/1998 | Darling, Jr. |
| 5,755,756 A | 5/1998 | Freedman, Jr. et al. |
| 5,779,631 A | 7/1998 | Chance |
| 5,782,755 A | 7/1998 | Chance et al. |
| 5,792,051 A | 8/1998 | Chance |
| 5,795,292 A | 8/1998 | Lewis et al. |
| 5,802,865 A | 9/1998 | Strauss |
| 5,807,263 A | 9/1998 | Chance |
| 5,820,558 A | 10/1998 | Chance |
| 5,827,222 A | 10/1998 | Klatz et al. |
| 5,836,993 A | 11/1998 | Cole |
| 5,837,003 A | 11/1998 | Ginsburg |
| 5,853,370 A | 12/1998 | Chance et al. |
| 5,860,292 A | 1/1999 | Augustine et al. |
| 5,871,526 A | 2/1999 | Gibbs et al. |
| 5,873,821 A | 2/1999 | Chance et al. |
| 5,899,865 A | 5/1999 | Chance |
| 5,902,235 A | 5/1999 | Lewis et al. |
| 5,913,885 A | 6/1999 | Klatz et al. |
| 5,916,242 A | 6/1999 | Schwartz |
| 5,917,190 A | 6/1999 | Yodh et al. |
| 5,954,053 A | 9/1999 | Chance et al. |
| 5,957,963 A | 9/1999 | Dobak, III |
| 5,964,092 A | 10/1999 | Tozuka et al. |
| 5,987,351 A | 11/1999 | Chance |
| 6,010,528 A | 1/2000 | Augustine et al. |
| 6,012,179 A * | 1/2000 | Garrett et al. ................. 2/456 |
| 6,030,412 A | 2/2000 | Klatz et al. |
| 6,044,648 A | 4/2000 | Rode |
| 6,058,324 A | 5/2000 | Chance |
| 6,090,132 A | 7/2000 | Fox |
| 6,091,989 A | 7/2000 | Swerdlow et al. |
| 6,101,413 A | 8/2000 | Olson et al. |
| 6,110,168 A | 8/2000 | Ginsburg |
| 6,119,474 A | 9/2000 | Augustine et al. |
| 6,126,680 A | 10/2000 | Wass |
| 6,141,584 A | 10/2000 | Rockwell et al. |
| 6,148,233 A | 11/2000 | Owen et al. |
| 6,149,624 A | 11/2000 | McShane |
| 6,149,670 A | 11/2000 | Worthen et al. |
| 6,149,673 A | 11/2000 | Ginsburg |
| 6,149,677 A | 11/2000 | Dobak, III |
| 6,156,007 A | 12/2000 | Ash |
| 6,156,057 A | 12/2000 | Fox |
| 6,183,501 B1 | 2/2001 | Latham |
| 6,188,930 B1 | 2/2001 | Carson |
| 6,209,144 B1 * | 4/2001 | Carter .......................... 2/458 |
| 6,248,126 B1 | 6/2001 | Lesser et al. |
| 6,269,267 B1 | 7/2001 | Bardy et al. |
| 6,277,143 B1 * | 8/2001 | Klatz et al. ................ 607/104 |
| 6,283,123 B1 | 9/2001 | Van Meter et al. |
| 6,303,156 B1 | 10/2001 | Ferrigno |
| 6,321,113 B1 | 11/2001 | Parker et al. |
| 6,325,818 B1 | 12/2001 | Werneth |
| 6,354,099 B1 | 3/2002 | Bieberich |
| 6,356,785 B1 | 3/2002 | Snyder et al. |
| 6,370,428 B1 | 4/2002 | Snyder et al. |
| 6,375,673 B1 | 4/2002 | Clifton et al. |
| 6,375,674 B1 | 4/2002 | Carson |
| 6,389,828 B1 | 5/2002 | Thomas |
| 6,402,775 B1 | 6/2002 | Bieberich |
| 6,406,427 B1 | 6/2002 | Williams et al. |
| 6,409,745 B1 | 6/2002 | Ducharme et al. |
| 6,416,480 B1 | 7/2002 | Nenov |
| 6,426,759 B1 | 7/2002 | Ting et al. |
| 6,432,124 B1 | 8/2002 | Worthen et al. |
| 6,451,045 B1 | 9/2002 | Walker et al. |
| 6,461,379 B1 * | 10/2002 | Carson et al. ............. 607/104 |
| 6,473,920 B1 * | 11/2002 | Augustine et al. ............. 5/423 |
| 6,487,871 B1 | 12/2002 | Augustine et al. |
| 6,497,358 B1 | 12/2002 | Walsh |

| | | |
|---|---|---|
| 6,497,720 B1 | 12/2002 | Augustine et al. |
| 6,497,721 B1 | 12/2002 | Ginsburg et al. |
| 6,508,831 B1 | 1/2003 | Kushnir |
| 6,511,502 B1 | 1/2003 | Fletcher |
| 6,516,224 B1 | 2/2003 | Lasersohn et al. |
| 6,519,964 B1 | 2/2003 | Bieberich |
| 6,520,933 B1 | 2/2003 | Evans et al. |
| 6,523,354 B1 | 2/2003 | Tolbert |
| 6,527,798 B1 | 3/2003 | Ginsburg et al. |
| 6,544,282 B1 | 4/2003 | Dae et al. |
| 6,547,811 B1 | 4/2003 | Becker et al. |
| 6,551,347 B1 | 4/2003 | Elkins |
| 6,551,348 B1 | 4/2003 | Blalock et al. |
| 6,551,349 B1 | 4/2003 | Lasheras et al. |
| 6,558,412 B1 | 5/2003 | Dobak, III |
| 6,558,413 B1 | 5/2003 | Augustine et al. |
| 6,576,002 B1 | 6/2003 | Dobak, III |
| 6,581,400 B1 | 6/2003 | Augustine et al. |
| 6,582,398 B1 | 6/2003 | Worthen et al. |
| 6,582,455 B1 | 6/2003 | Dobak, III et al. |
| 6,599,312 B1 | 7/2003 | Dobak, III |
| 6,607,517 B1 | 8/2003 | Dae et al. |
| 6,610,083 B1 | 8/2003 | Keller et al. |
| 6,620,187 B1 | 9/2003 | Carson et al. |
| 6,620,188 B1 | 9/2003 | Ginsburg et al. |
| 6,620,189 B1 | 9/2003 | Machold et al. |
| 6,623,516 B1 | 9/2003 | Saab |
| 6,635,076 B1 | 10/2003 | Ginsburg |
| 6,645,232 B1 | 11/2003 | Carson |
| 6,645,234 B1 | 11/2003 | Evans et al. |
| 6,656,208 B1 | 12/2003 | Grahn et al. |
| 6,656,209 B1 | 12/2003 | Ginsburg |
| 6,682,550 B1 | 1/2004 | Clifton et al. |
| 6,692,518 B1 * | 2/2004 | Carson ................... 607/104 |
| 6,697,671 B1 | 2/2004 | Nova et al. |
| 6,800,087 B1 | 10/2004 | Papay et al. |
| 6,813,517 B1 | 11/2004 | Daynes et al. |
| 6,829,501 B1 | 12/2004 | Nielsen et al. |
| 6,887,199 B1 | 5/2005 | Bridger et al. |
| 2001/0021866 A1 | 9/2001 | Dobak, III et al. |
| 2001/0027333 A1 | 10/2001 | Schwartz |
| 2001/0027334 A1 | 10/2001 | White |
| 2001/0039439 A1 | 11/2001 | Elkins et al. |
| 2001/0049545 A1 | 12/2001 | Lasersohn et al. |
| 2001/0051801 A1 | 12/2001 | Lehmann et al. |
| 2002/0002394 A1 | 1/2002 | Dobak, III |
| 2002/0004729 A1 | 1/2002 | Zak et al. |
| 2002/0007201 A1 | 1/2002 | Grahn et al. |
| 2002/0026226 A1 | 2/2002 | Ein |
| 2002/0029073 A1 | 3/2002 | Schwartz |
| 2002/0032473 A1 | 3/2002 | Kushnir et al. |
| 2002/0072785 A1 | 6/2002 | Nelson et al. |
| 2002/0091428 A1 | 7/2002 | Larnard et al. |
| 2002/0091431 A1 | 7/2002 | Gunn et al. |
| 2002/0095200 A1 | 7/2002 | Dobak, III et al. |
| 2002/0095201 A1 | 7/2002 | Worthen et al. |
| 2002/0099427 A1 | 7/2002 | Dobak, III |
| 2002/0103508 A1 | 8/2002 | Mathur |
| 2002/0103520 A1 | 8/2002 | Latham |
| 2002/0116041 A1 | 8/2002 | Daoud |
| 2002/0120317 A1 | 8/2002 | Fletcher |
| 2002/0138302 A1 | 9/2002 | Bodnick |
| 2002/0151946 A1 | 10/2002 | Dobak, III |
| 2002/0183815 A1 | 12/2002 | Nest et al. |
| 2002/0183816 A1 | 12/2002 | Tzeng et al. |
| 2002/0193852 A1 | 12/2002 | Renfro |
| 2002/0193853 A1 | 12/2002 | Worthen et al. |
| 2002/0193854 A1 | 12/2002 | Dobak, III et al. |
| 2002/0193855 A1 | 12/2002 | Dobak, III |
| 2002/0198578 A1 | 12/2002 | Dobak, III |
| 2003/0018375 A1 | 1/2003 | Dobak, III et al. |
| 2003/0023288 A1 | 1/2003 | Magers |
| 2003/0036786 A1 | 2/2003 | Duren et al. |
| 2003/0040782 A1 | 2/2003 | Walker et al. |
| 2003/0040783 A1 | 2/2003 | Salmon |
| 2003/0055472 A1 | 3/2003 | Worthen |
| 2003/0055473 A1 | 3/2003 | Ramsden et al. |
| 2003/0060863 A1 | 3/2003 | Dobak, III |
| 2003/0060864 A1 | 3/2003 | Whitebrook et al. |
| 2003/0066304 A1 | 4/2003 | Becker et al. |
| 2003/0078638 A1 | 4/2003 | Voorhees et al. |
| 2003/0078639 A1 | 4/2003 | Carson |
| 2003/0078640 A1 | 4/2003 | Carson et al. |
| 2003/0083000 A1 | 5/2003 | Vester |
| 2003/0083721 A1 | 5/2003 | Larnard |
| 2003/0088299 A1 | 5/2003 | Magers et al. |
| 2003/0114903 A1 | 6/2003 | Ellingboe |
| 2003/0135252 A1 | 7/2003 | MacHold et al. |
| 2003/0144714 A1 | 7/2003 | Dobak, III |
| 2003/0150545 A1 | 8/2003 | Szczesuil et al. |
| 2003/0195597 A1 | 10/2003 | Keller et al. |
| 2003/0216799 A1 | 11/2003 | Worthen et al. |
| 2003/0225336 A1 | 12/2003 | Callister et al. |
| 2004/0158303 A1 | 8/2004 | Lennox et al. |

FOREIGN PATENT DOCUMENTS

| | | |
|---|---|---|
| GB | 764993 | 1/1957 |
| JP | 8084744 | 4/1996 |
| JP | 9182766 | 7/1997 |
| JP | 9220251 | 8/1997 |
| JP | 10258080 | 9/1998 |
| JP | 10277080 | 10/1998 |
| WO | WO 99/08632 | 2/1999 |
| WO | WO 99/23980 A1 | 5/1999 |
| WO | WO 99/23989 A1 | 5/1999 |
| WO | WO 99/44552 A1 | 9/1999 |
| WO | WO 00/33236 A1 | 6/2000 |
| WO | WO 01/95977 A1 | 12/2001 |
| WO | WO 02/41231 A2 | 5/2002 |

OTHER PUBLICATIONS

Sophie Cluet and Claude Delobel, "A General Framework for the Optimization of Object-Oriented Queries," ACM SIGMOD Record vol. 21, Issue 2, pp. 383-392 (Jun. 1992).

Written Opinion dated Oct. 12, 2004 for corresponding Application No. PCT/US03/30695 (5 pages).

US 6,645,236, 11/2003, Lachenbruch et al. (withdrawn)

* cited by examiner

FEEDBACK SYSTEM FOR RAPID INDUCTION OF MILD HYPOTHERMIA

TECHNICAL FIELD

The invention relates to medical devices that control the temperature of a patient, and more particularly, to feedback systems for medical devices that control the temperature of a patient.

BACKGROUND

Some medical conditions may be treated by hypothermia. In many cases, hypothermic therapy within the first few minutes of the onset of a condition may mean the difference between life and death. In some cases in which the patient is spared death, prompt hypothermic therapy may make a dramatic difference in the quality of life of the patient.

Stroke is an example of a medical condition that may be treated by prompt administration of hypothermic therapy. Many patients that suffer strokes die as a result of the stroke, and a significant fraction of those who survive suffer some degree of neurological damage. The neurological damage to the patient may be slowed by the application of hypothermic therapy.

There have been many different techniques studied to produce hypothermia in the body, including invasive and non-invasive techniques, such as the use of cold packs, ice blankets, injecting a cooled saline solution into the blood stream, heating the hypothalamus, cooling the air around the patient, and circulating of a coolant fluid around the patient. Some techniques are more effective than others. Many of these techniques involve bulky apparatuses that are difficult to transport to the patient, and are usually available only in a hospital setting. In addition, many of these techniques rely upon the training of specially skilled hospital personnel. There may be a significant delay in administration of hypothermic therapy while the patient is being taken to the hospital.

SUMMARY

In general, the invention is directed to techniques for control of a cooling garment using a cooling feedback system. In particular, a feedback system may control a cooling garment in response to a signal from the sensor. The sensor may be placed within the cooling garment, and may generate a signal as a function of a patient parameter such as body temperature, and/or heart rate. The cooling garment may include sensors within more than one of the garments. Also, a cooling garment may contain more than one sensor. A controller may receive signals from the sensors via a communication bundle. The controller may compare the signals received from the sensors with target values input by a user, usually emergency medical personnel or a doctor. When the received signals are outside of an appropriate operating range, the controller may send a regulation signal to a regulator. The regulator may adjust delivery of one or more of a coolant, a carrier gas, and/or a warm air supply to the cooling garment. For instance, the regulator may adjust the pressure of the coolant, the temperature of the coolant, the flow rate of the coolant, and/or the mixing ratio of the coolant. The regulator may also adjust the delivery of the carrier gas and the warm air supply concurrently with the coolant.

In one embodiment, the invention is directed to a system that comprises a cooling garment that contacts a portion of the body of a patient. The cooling garment delivers a coolant and a carrier gas to the body of the patient. The system further comprises a controller for controlling the cooling garment in response to a signal from a sensor.

In another embodiment, the invention presents a method comprising delivering a carrier gas and a coolant to a cooling garment in contact with the body of a patient. The method further comprises generating a signal that measures a parameter of the body of the patient. The method also includes controlling the cooling garment in response to the generated signal.

In another embodiment, the invention presents a system that comprises a coolant supply that supplies coolant to a cooling garment that contacts a portion of a body of a patient. The system also comprises a carrier gas supply that supplies carrier gas to the cooling garment. The system includes a warm air supply that supplies warm air to a body part of the patient. The system also includes a regulator that regulates at least one of the coolant supply, the carrier gas supply and the warm air supply as a function of a patient parameter.

The invention may provide numerous advantages. The feedback system may provide for a safe yet rapid lowering of the temperature of the patient, by continuously monitoring the condition of the patient. Should the patient be at risk of frostbite, for example, the system may automatically perform adjustments to reduce that risk. In addition, the system may respond to conditions other than temperature, and may regulate therapy as a function of those conditions. The system may further alert a health care professional of life-threatening conditions, such as a serious arrhythmia or cardiac arrest.

In addition, the feedback system may regulate one or more cooling garments simultaneously. Each garment may be regulated individually for enhanced effect. Regulation of multiple garments allows the garments to work together in concert.

Furthermore, the feedback system is versatile and can be customized to the needs of each patient. A user may program the system to supply appropriate therapy for the patient.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
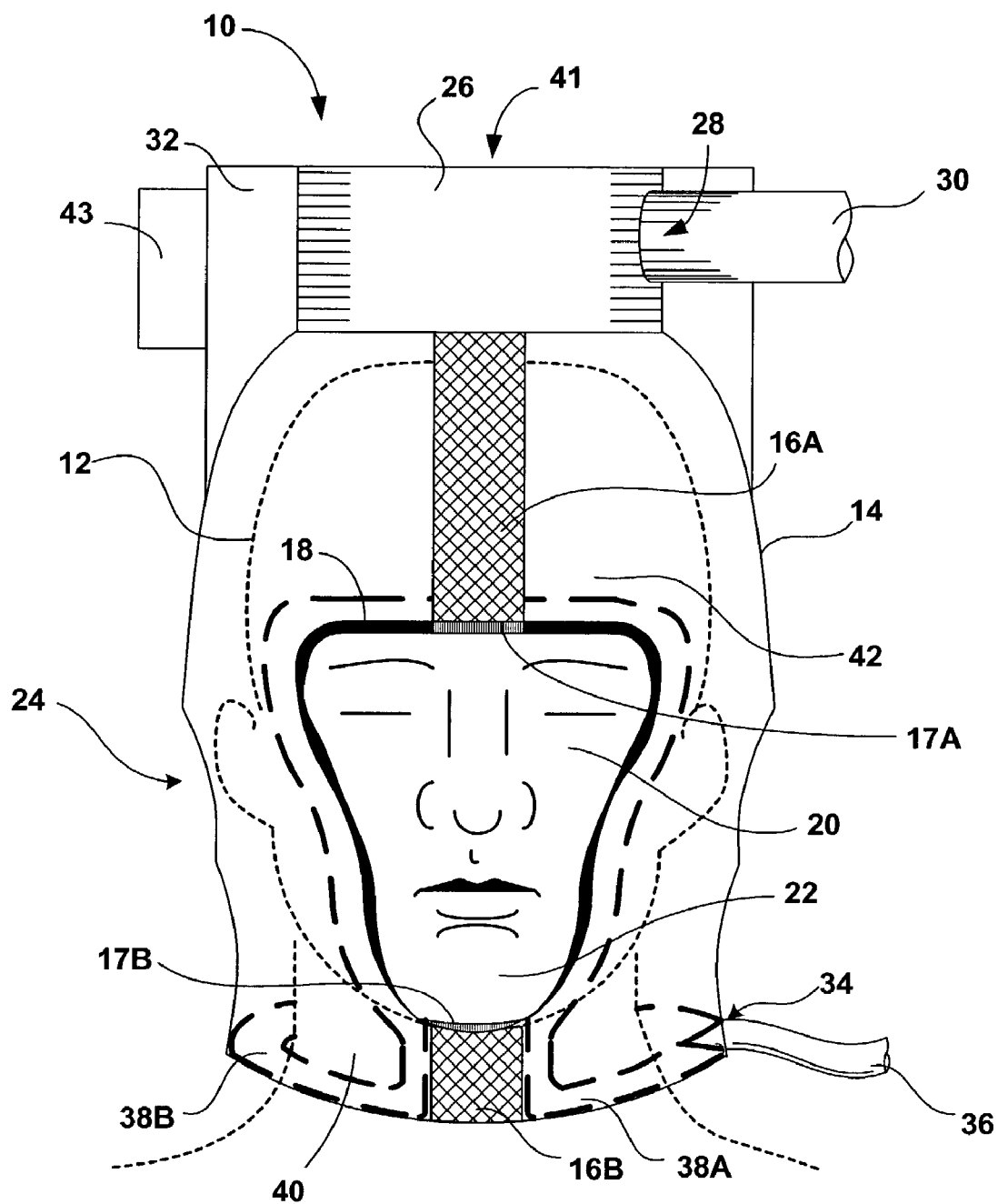
FIG. 1 is a schematic diagram illustrating a front view of an exemplary headgear used for cooling of a patient, according to an embodiment of the invention.

FIG. 1 is a schematic front view of an exemplary headgear 10 used for cooling of a patient 12. Headgear 10 is one embodiment of a cooling garment. Headgear 10 comprises a deformable enclosure member 14. Enclosure member 14 deforms so that enclosure member 14 may be placed upon the head of patient 12. Enclosure member 14 includes one or more spacers (not shown) that separate at least a portion of enclosure member 14 from the body of patient 12 defining a space. A spacer may be coupled to headgear 10. Alternatively, a spacer may detach from headgear 10.

Once placed upon the head of patient 12, enclosure member 14 may be held in place with fasteners 16A and 16B (collectively fasteners 16), allowing a user, such as emergency medical personnel to administer other treatments to patient 12. Fastener 16A adjusts just above face 20 and fastener 16B adjusts under chin 22, so as to fit around different size heads. Securing fasteners 16 causes seal members 17A and 17B (collectively seal members 17) to contact the body of patient 12, substantially isolating the space inside enclosure member 14 from an exterior environment.

Enclosure member 14 may be formed from a substantially compliant material, such as rubber, plastic, or airtight cloth. Enclosure member 14 may have a different rigidity for an anterior portion as opposed to a posterior portion. For example, the posterior of enclosure member 14 may be more rigid in order to support the weight of patient 12. Seal members 17 may be formed from a pliable material such as rubber, plastic, or silicone, and may be sewn, bonded, or otherwise affixed to enclosure member 14. Seal member 17, for example, may be a flexible rubber web, an 0-ring tube seal, a collapsible tube or the like. Fasteners 16 may be any sort of fastening device such as a zipper, a hook and loop fastener such as VELCRO, a button, a clip, a buckle, a strap, an adhesive, or the like.

Enclosure member 14 may include an ear access 24, which allows outside access to the ear of patient 12 when headgear 10 is in place on the head. The temperature of patient 12 may be measured through ear access 24. Ear access 24 may be embodied as an aperture in enclosure member 14, an earflap, or the like. Enclosure member 14 may further include other body accesses that allow access to other portions of the head.

Headgear 10 further comprises a gas intake/outflow unit 26. Gas intake/outflow unit 26 may include a carrier gas intake port 28 that receives a carrier gas supply 30. Gas intake/outflow unit 26 may be substantially rigid, and may be formed from materials such as non-corrosive metal, plastic, or rubber. Gas intake/outflow unit 26 and, more particularly, carrier gas intake port 28, fluidly connects the space between the head of patient 12 and enclosure member 14 to carrier gas supply 30. In general, gas intake/outflow unit 26 receives a carrier gas from carrier gas supply 30. A carrier gas mover (not shown) moves the carrier gas within the space. The operation of gas intake/outflow unit 26 will be described in more detail below. The carrier gas may be carbon dioxide, nitrogen, air or the like. Alternatively, the carrier gas may be a mixture of gases. For example, the carrier gas may be a mixture of carbon dioxide and air. In one instance, air may be mixed with the carbon dioxide to reduce the temperature of the carrier gas for the safety of the patient. Carrier gases such as carbon dioxide and nitrogen may be more effective than air in absorbing evaporated coolant, especially in an environment with high humidity. For reasons of safety, the carrier gas may be a gas other than oxygen and non-reactive with oxygen.

Headgear 10 may further include a coolant port 34 that receives a coolant supply 36. Coolant port 34 brings coolant supply 36 into fluid communication with a coolant delivery conduit 38. Coolant delivery conduit 38 may branch at coolant port 34 into coolant delivery conduit branch 38A and 38B. Coolant delivery conduit branch 38A may carry a liquid coolant into headgear 10, anteriorly to approximately under chin 22, around left side of face 20 of patient 12, and to the edge of fastener 16A. Coolant delivery conduit branch 38B may carry the liquid coolant posteriorly around neck 40 of patient 12, then anteriorly to approximately under chin 22, around right side of face 20, and to the edge of fastener 16A. In particular, coolant delivery conduit 38 may extend from coolant port 34 posteriorly around neck 40 to approximately under chin 22 in both directions. Coolant delivery conduit 38 may proceed from chin 22 around face 20 and terminate at two sites proximate to fastener 16A. The invention encompasses coolant delivery conduit 38 branching in a fashion different than described above, or not branching at all.

The pressure of the coolant in coolant delivery conduit 38 may form a seal member 18 for the portions of headgear 10 around neck 40 and face 20. In other words, coolant delivery conduit 38 may transport coolant around the head and form a seal proximate to face 20. Seal members 17 create the seal at sites around face 20 where coolant delivery conduit 38 does not extend. Alternatively, coolant delivery conduit 38 may not be a seal member, in which case seal members 17 may create the seal around face 20. Coolant delivery conduit 38 and/or seal members 17 may also be a spacer that creates the space between the patient and headgear 10.

Coolant delivery conduit 38 may be flexibly formed from tube-like structures made of materials such as rubber, plastic, or the like. Coolant delivery conduit 38 may be shaped to expand and contract to accommodate heads of different sizes and shapes. Examples of construction of coolant delivery conduit 38 will be described in more detail below.

Coolant supply 36 is a tube-like structure, which may allow one-way or two-way flow of the coolant. Coolant supply 36 may be constructed of flexible tube-like structures made of materials such as rubber, plastic, silicone or the like. Coolant supply 36 may include a quick-connect coupling (not shown) that mates to coolant port 34. In a typical application, coolant supply 36 may be coupled to coolant port 34 after headgear 10 is placed upon the head of patient 12.

Coolant delivery conduit 38 may include small apertures (not shown) that allow the coolant to drip out, seep out, mist out, spray out, or otherwise exit the lumen of coolant delivery conduit 38. In the example of FIG. 1, the coolant that exits from coolant delivery conduit 38 may be applied to the body of patient 12. For example, the coolant that exits coolant delivery conduit 38 may be applied to an absorbent layer in contact with the body. The absorbent layer absorbs the coolant and keeps the coolant in contact with the body. The absorbent layer may further prevent the coolant from pooling up in areas where gravity tends to pull the coolant. The absorbent layer may be constructed of material such as polypropylene, cotton, or the like. The coolant may also be applied directly to the body of patient 12. Although in this embodiment the liquid coolant is applied to the body of patient 12, the invention may further include applying the liquid coolant inside the headgear in other fashions. For example, the coolant that exits from coolant delivery conduit 38 may also mix with the carrier gas from carrier gas supply 30. Liquid coolant need not come in direct contact with the body of patient 12.

The coolant is typically a liquid that evaporates due to the heat generated by the head of patient 12 or by a gas flowing over the coolant. Alcohol, water, or a mixture of alcohol and water are examples of typical coolants. However, the coolant may also be a gas or a gel. Liquid coolants accept heat and undergoes a state change to gaseous form. This heat of transformation can be substantial. The state change of the coolant inside of headgear 10 draws body heat and thereby cools patient 12. Coolant applied to the body of patient 12 may draw body heat from direct contact of the coolant and patient 12 through this evaporation process. If the coolant that is applied within headgear 10 is not applied directly to the body, such as the example of mixing coolant with a carrier gas, the coolant may draw body heat from direct contact of the coolant and patient 12 or from heat propagating outward from patient 12 by radiation or convection. Carrier gas and coolant in gaseous form are discharged through an exit port 41 located within gas intake/outflow unit 26 as will be described below, and fresh carrier gas and coolant replace what has been discharged.

Headgear 10 may include multiple coolant delivery conduits, multiple gas intake ports or both. Multiple conduits and intake ports may allow for localized cooling of portions of the head. For example, headgear 10 may include four cooling areas. Each cooling area may be served by a discrete coolant delivery conduit 38 and a gas intake port 28. Alternatively, each cooling area may include a common coolant delivery conduit 38 and separate gas intake port 28. The cooling areas may be separated from one another by one or more dividers that isolate the space of one cooling area from the space of neighboring cooling areas. The same coolant supply 36, may supply coolant to each of the coolant delivery conduits. Alternatively, a separate coolant supply 36 may supply coolant to each of the coolant delivery conduits. Carrier gas intake ports 28 may also be supplied by the same carrier gas supply or multiple carrier gas supplies.

As will be described below, a housing 32 may house a processor to process information that the processor receives from optical fiber links, a wireless link, wire link, and the like. For example, the processor may receive information in the form of signals from one or more sensors on the body of patient 12. Headgear 10 may further comprise a battery pack 43 that operates headgear 10 when no AC power source is available. For example, battery pack 43 may power the processor at the location of a traumatic event. Battery pack 43 may also power the carrier gas mover or any other electric or electronic components of headgear 10. In this manner, headgear 10 may be powered by any source, including an alternating current (AC) power source and a direct current (DC) power source.

Figure 2:
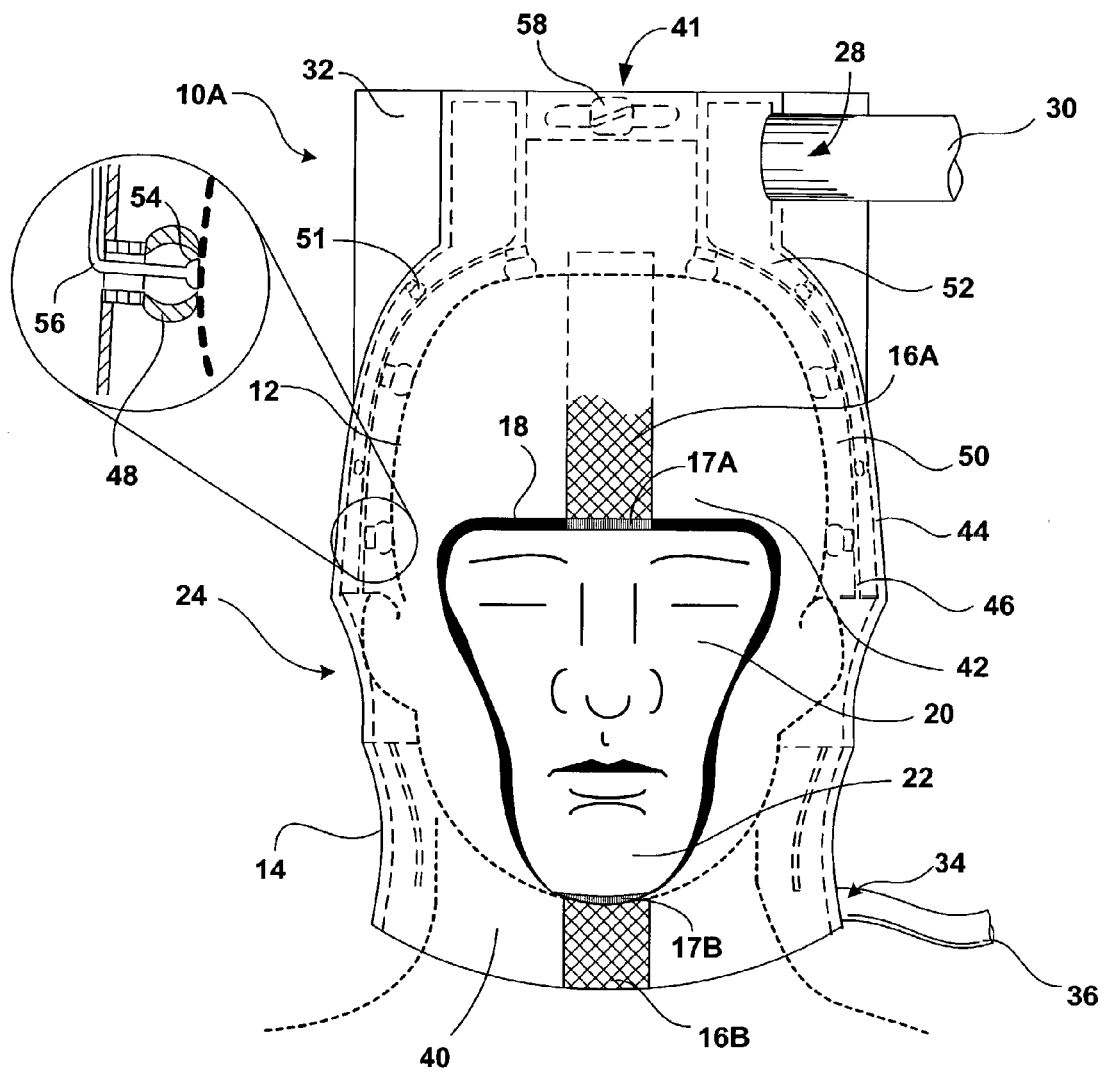
FIG. 2 is a schematic diagram illustrating a front view of an embodiment the headgear shown in FIG. 1.

FIG. 2 is a schematic front view of an embodiment of headgear 10 of FIG. 1. Headgear 10A may further comprise an outer shell 44 and an inner shell 46. A set of inner spacers 48 creates a separation between patient 12 and inner shell 46, the separation between patient 12 and inner shell 46 referred to hereinafter as an inner space 50. A set of outer spacers 51 creates a separation between outer shell 44 and inner shell 46, the separation outer shell 44 and inner shell 46 referred to hereinafter as an outer space 52. Inner space 50 is in fluid communication with outer space 52. Inner shell 46 may be constructed from a rigid to semi-rigid material such as a plastic, rubber or the like. Outer shell 44 may be constructed from a rigid to semi-rigid material that is also electrically insulated such as plastic, rubber, or the like. Outer shell 44 may be constructed from a rigid to semi-rigid material that is also electrically insulated. Insulation of outer shell 44 may prevent interference with electrical equipment concurrently being used for treatment and monitoring of patient 12. Inner spacers 48 and outer spacers 51 may be constructed from materials such as plastic, rubber, or the like. Alternatively, spacers 48 and 51 may be a chain, air, or the like.

Inner spacers 48 may house within them at least one sensor 54 and a communication link 56. Sensor 54 generates a signal as a function of a patient parameter such as temperature, oxygen saturation levels, blood flow, heart rate, brain electrical action, end tidal carbon dioxide levels or the like. Communication link 56 then relays the signal to a processor, which may be housed in housing 32. Sensor 54 may be an assortment of sensor devices such as a temperature sensor, a thermocouple, an oxygen sensor, a velocity Doppler probe, an electrocardiogram (ECG) sensor, an electroencephalograph (EEG) sensor, or the like. Communication link 56 may include an optical fiber link, a wireless link, a wire link, or the like.

Carrier gas entering headgear 10A at carrier gas port 28 enters outer space 52 in gas intake/outflow unit 26. Carrier gas flows in outer space 52 from the crown of the head toward the neck, where carrier gas enters inner space 50. Carrier gas flows in inner space 50 from the neck to the crown, exiting at exit port 41 in gas intake/outflow unit 26. Gas intake/outflow unit 26 may include a carrier gas mover, such as a fan 58, that circulates carrier gas within headgear 10A. Other carrier gas movers, such as a pressurized carrier gas supply or a pump, may be used to move the carrier gas instead of or in addition to fan 58.

Figure 3:
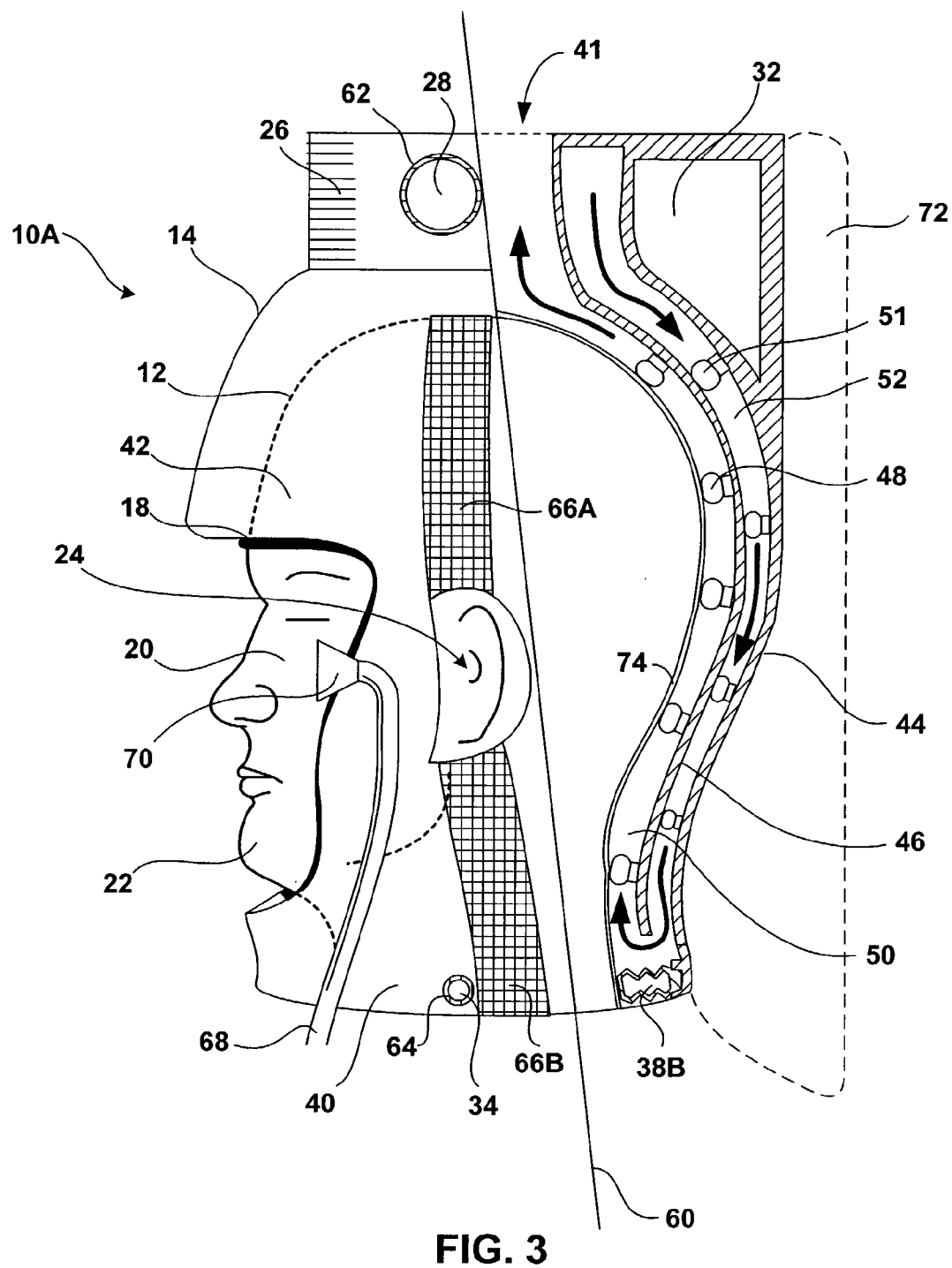
FIG. 3 is a schematic diagram illustrating a split cross-sectional profile of the exemplary headgear of FIG. 2.

FIG. 3 is a schematic diagram illustrating a split cross-sectional profile of exemplary headgear 10A of FIG. 2. The outer profile of headgear 10A is shown to the left of line 60 and the inner cross-sectional profile of headgear 10A is shown to the right of line 60.

Headgear 10A may comprise a gas fitting 62 mated to carrier gas port 28. Gas fitting 62 may be a quick-connect coupling that mates carrier gas supply 30 to gas intake/outflow unit 26. Headgear 10A may further comprise a coolant fitting 64. Coolant fitting 64 may be a quick-connect coupling that mates coolant supply 36 to coolant port 34.

Headgear 10A may also comprise expanders 66A and 66B (collectively expanders 66). Expanders 66 allow headgear 10A to expand to accommodate different sizes and shapes of heads. As mentioned previously, the material of headgear 10A may be more rigid posteriorly from expanders 66 to the back of the head of patient 12 than anteriorly from expanders 66 to the face 20 of patient 12. Expanders 66 may be constructed from a material with the ability to stretch and contract, such as spandex, rubber, elastic or the like.

Headgear 10A may further comprise a warm air supply 68 and a warm air nozzle 70 to blow warm air on face 20 of patient 12. When patient 12 undergoes cooling, patient 12 may shiver. Shivering generates heat and is counterproductive to the cooling process. Warm air applied via warm air nozzle 70 to face 20 may reduce shivering. In addition, warm air supply 68 and warm air nozzle 70 may be applied with enough pressure to blow coolant and carrier gas that may leak from headgear 10A away from the eyes, nose, or mouth of patient 12. Warm air supply 68 may be made of a tube-like structure made of materials such as rubber, plastic, or the like. Warm air nozzle 70 receives warm air from warm air supply 68, and may spread the warm air to cover a substantial portion of face 20.

Headgear 10A may also comprise a support pad 72 to support the head of patient 12. Since patient 12 will be lying for most of the monitoring and treatment procedures, support pad 72 will give patient 12 some level of comfort. Furthermore, support pad 72 may prevent wear to the backside of headgear 10A from friction between the ground and headgear 10A. Support pad 72 may be any type of padding such as a pillow, a cushion, and the like. Support pad 72 of FIG. 3 is shown as an extension from outer shell 44. Alternatively, support pad 72 may be located within headgear 10A, and may further be absorbent to collect excess coolant to prevent the coolant from pooling up in areas where gravity tends to pull the coolant, such as the back of the head and neck.

The inner profile of headgear 10A, shown to the right of line 60, illustrates how headgear 10A circulates carrier gas. Carrier gas supply 30 is coupled to gas port 28 via gas fitting 62. The carrier gas from carrier gas supply 30 enters outer space 52 in gas intake/outflow unit 26.

Coolant supply 36 is coupled to coolant port 34 via cooling fitting 64. The coolant from coolant supply 36 enters headgear 10A and is carried by coolant delivery conduit 38. Coolant delivery conduit 38 branches proximate to coolant port 34, and coolant delivery conduit branch 38B carries coolant posteriorly around the neck.

A cross-section of coolant delivery conduit branch 38B is shown in FIG. 3. In the embodiment shown in FIG. 3, coolant delivery conduit 38 has a pleated cross-section that allows coolant delivery conduit 38 to conform to different sizes of necks.

Small apertures in coolant delivery conduit 38 may allow the coolant to drip out, mist out, seep out, spray out, or otherwise exit the lumen of cooling conduit 38 throughout the entire path of cooling conduit 38. In the example of FIG. 3, the coolant exits the lumen of cooling conduit 38 via small apertures and is applied to an absorbent layer 74 that is in contact with the head of patient 12. For example, the coolant may exit cooling conduit 38 around the face 20, and the coolant may migrate within the absorbent layer down the sides of the head. The absorbent material absorbs the coolant preventing the coolant from pooling in areas of the body, such as the back of the head. Although this embodiment applies the coolant from coolant delivery conduit 38 directly to the body of patient 12, the invention encompasses variants of applying coolant within headgear 10A such as carrying the coolant exiting the lumen of coolant delivery conduit 38 with a carrier gas.

Circulation created by a carrier gas mover, such as fan 58, may cause the carrier gas to flow from crown toward neck in outer space 52, and enter inner space 50 proximate to the neck. The coolant accepts heat from direct contact with patient 12 and evaporates. The evaporation and associated convection cools patient 12. Carrier gas and coolant in gaseous form are discharged through exit port 41 of gas intake/outflow unit 26.

Figure 4:
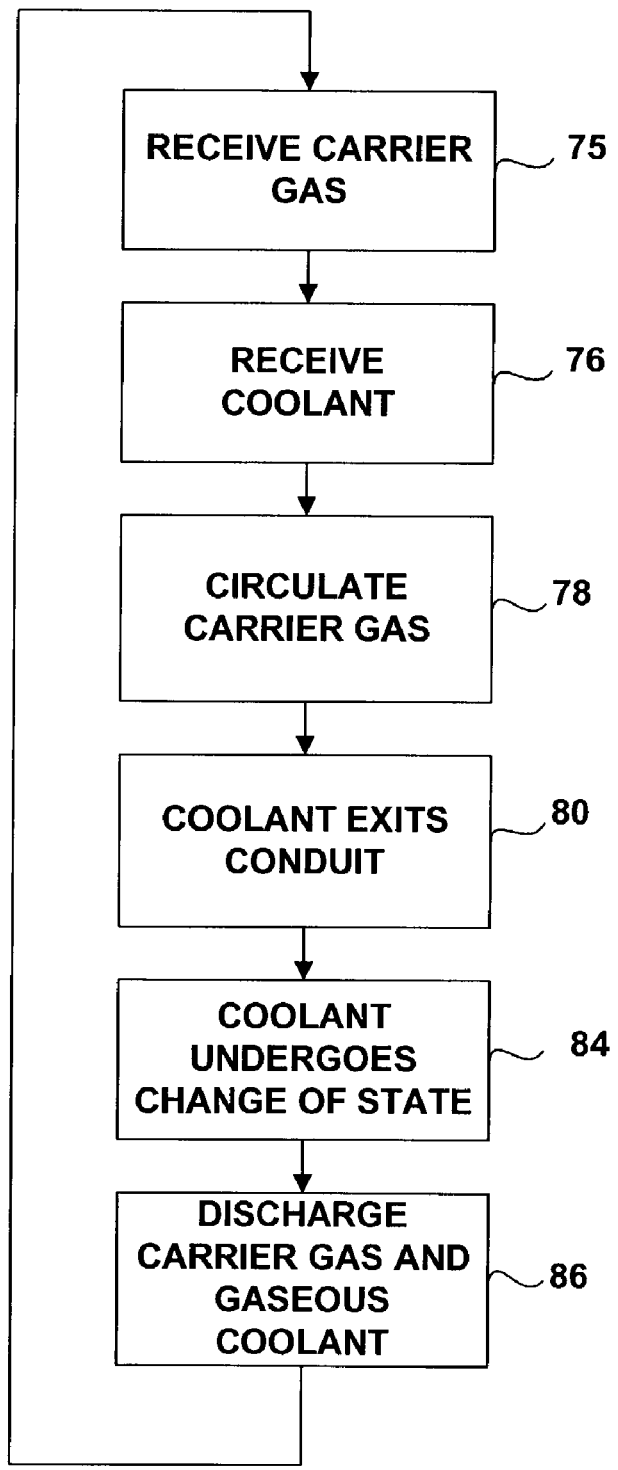
FIG. 4 is a flow diagram illustrating the cooling process occurring inside the headgear of FIG. 2.

FIG. 4 is a flow diagram illustrating the cooling process occurring inside headgear 10A. Headgear 10A and, more particularly, outer space 52 receives a carrier gas from carrier gas supply 30 (75). The incoming carrier gas may be dehumidified to enhance the evaporative cooling process. Further, the incoming carrier gas may be cooled using a carrier gas cooler such as a blue ice canister or a heat exchanger in order to enhance the evaporative cooling process.

Coolant delivery conduit 38 of headgear 10A further receives a coolant from coolant supply 36 via coolant port 64 (76). The coolant may be any kind of liquid such as water, alcohol, or a mixture of the two. Alcohol or an alcohol-water mixture may be a more effective coolant than water because alcohol evaporates more readily than water and can vaporize at cooler temperatures.

A carrier gas mover circulates the carrier gas inside headgear 10A. In FIGS. 2 and 3, for example, fan 58 or the carrier gas pressure moves the carrier gas through outer space 52 and inner space 50 (78). The carrier gas mover may increase the speed of circulation of the carrier gas to enhance the effectiveness of the evaporation process. Further, the size of inner space 50 and outer space 52 may further affect the effectiveness of the evaporation process. For example, an increase in gap size increases the effectiveness of the evaporation process.

Coolant conduit 38 allows the liquid coolant to escape from the lumen of coolant conduit 38 via small apertures (80). The liquid coolant may exit the lumen of coolant delivery conduit 38 throughout the entire path of coolant delivery conduit 38. Alternatively, the liquid coolant may exit the lumen of coolant delivery conduit 38 throughout portions of the path of coolant delivery conduit 38. Liquid coolant may exit the lumen of coolant delivery conduit 38 by, for example, dripping out, spraying out, seeping out, or misting out.

Coolant delivery conduit 38 brings the coolant into contact with the body of patient 12. The coolant may contact the body in absorbent layer 74 or may be applied directly to the body of patient 12. Heat from the body causes the coolant to undergo a state change (84), i.e., to evaporate. The evaporation and associated convection cools patient 12. The associated convection may dominate the cooling in the early stages of the process, whereas the evaporation may dominate the cooling in later stages of the cooling process as the body temperature of patient 12 begins to become closer to the temperature of the carrier gas.

In FIGS. 2 and 3, the circulating carrier gas encounters evaporated coolant principally in inner space 50. The circulating carrier gas carries the coolant in gaseous form away from patient 12. In FIGS. 2 and 3, the carrier gas carries the evaporated coolant in inner space 50 toward the crown. The carrier gas and gaseous coolant are discharged out through exit port 41 of gas intake/outflow unit 26 (86). Fresh carrier gas and coolant replace what has been discharged.

Figure 5:
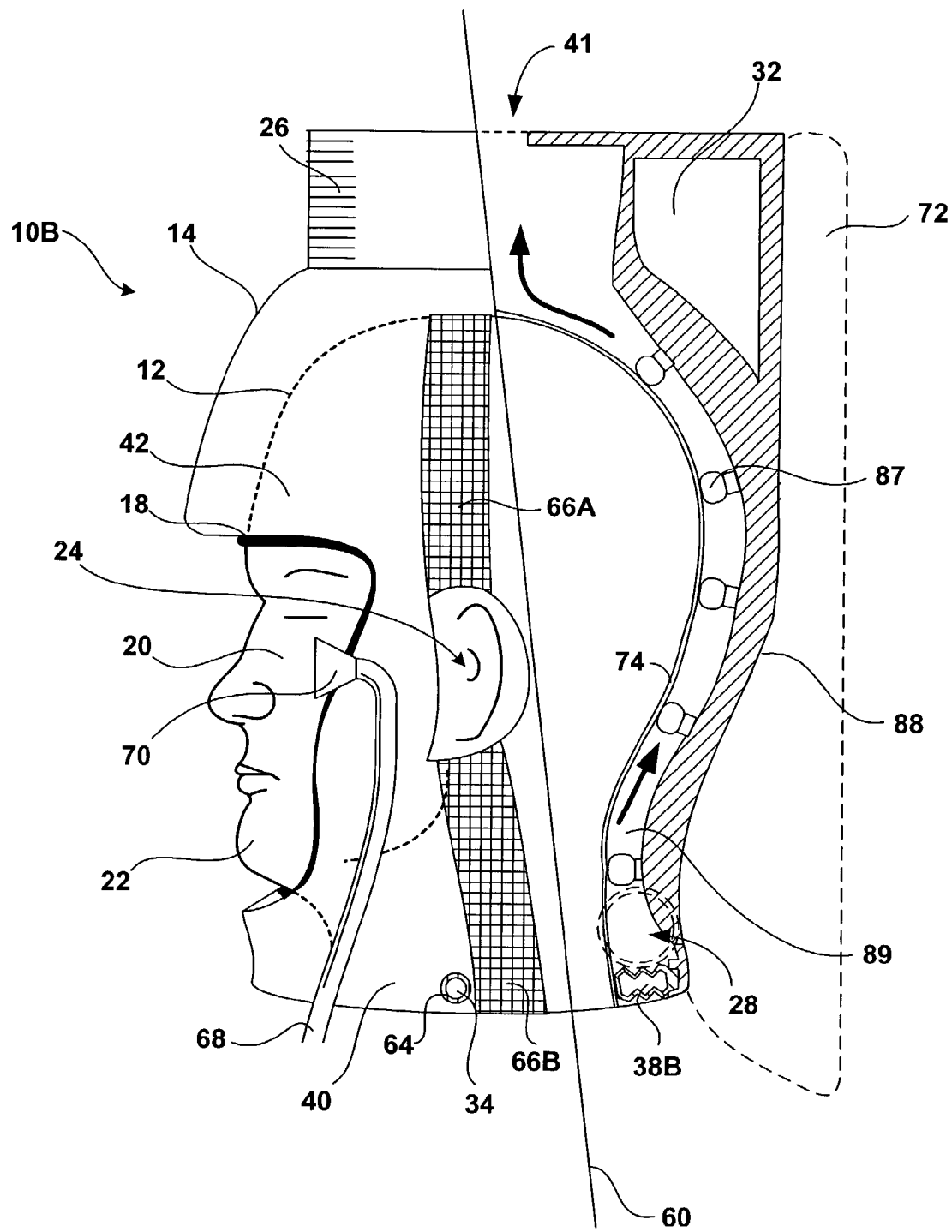
FIG. 5 is a schematic diagram illustrating a cross-sectional view of another embodiment of the headgear of FIG. 1.

FIG. 5 is a schematic diagram illustrating a cross-sectional view of another embodiment of headgear 10 of FIG. 1. Headgear 10B is similar to headgear 10 of FIG. 1, but carrier gas intake 28 of headgear 10B receives a carrier gas near the bottom portion proximate to the neck of patient 12. Carrier gas intake 28 may be proximate to coolant port 34, for example. Headgear 10B may further comprise a shell 88.

A set of spacers 87 creates a separation between patient 12 and shell 88, the separation between patient 12 and shell 88 referred to hereinafter as head space 89. Shell 88 may be constructed from a rigid material that is also electrically insulated such as a rigid plastic, rubber or the like. Spacers 87 may be constructed from materials such as plastic, rubber, or the like. Alternatively, spacers 87 may be a chain, air, or the like.

Spacers 87 may house within them at least one sensor and a communication link (neither shown in FIG. 5), similar to spacers 54 of headgear 10A. The sensor generates a signal as a function of a patient parameter such as temperature, oxygen saturation levels, blood flow, heart rate, brain electrical action, end tidal carbon dioxide levels or the like. The communication link then relays the signal to a processor, which may be housed in housing 32. The sensor may be an assortment of sensor devices such as a temperature sensor, a thermocouple, an oxygen sensor, a velocity Doppler probe, an electrocardiogram (ECG) sensor, an electroencephalograph (EEG) sensor, or the like. The communication link may include an optical fiber link, a wireless, a wire link, or the like.

Carrier gas entering headgear 10B at carrier gas port 28 enters head space 89. Carrier gas flows in head space 89 from the neck toward the crown of the head, exiting at exit port 41. Headgear 10B may include a carrier gas mover, such as fan 58 of FIG. 2, that circulates carrier gas within headgear 10B. Other carrier gas movers, such as a pressurized carrier gas supply or a pump, may be used to move the carrier gas instead of or in addition to fan 58.

Figure 6:
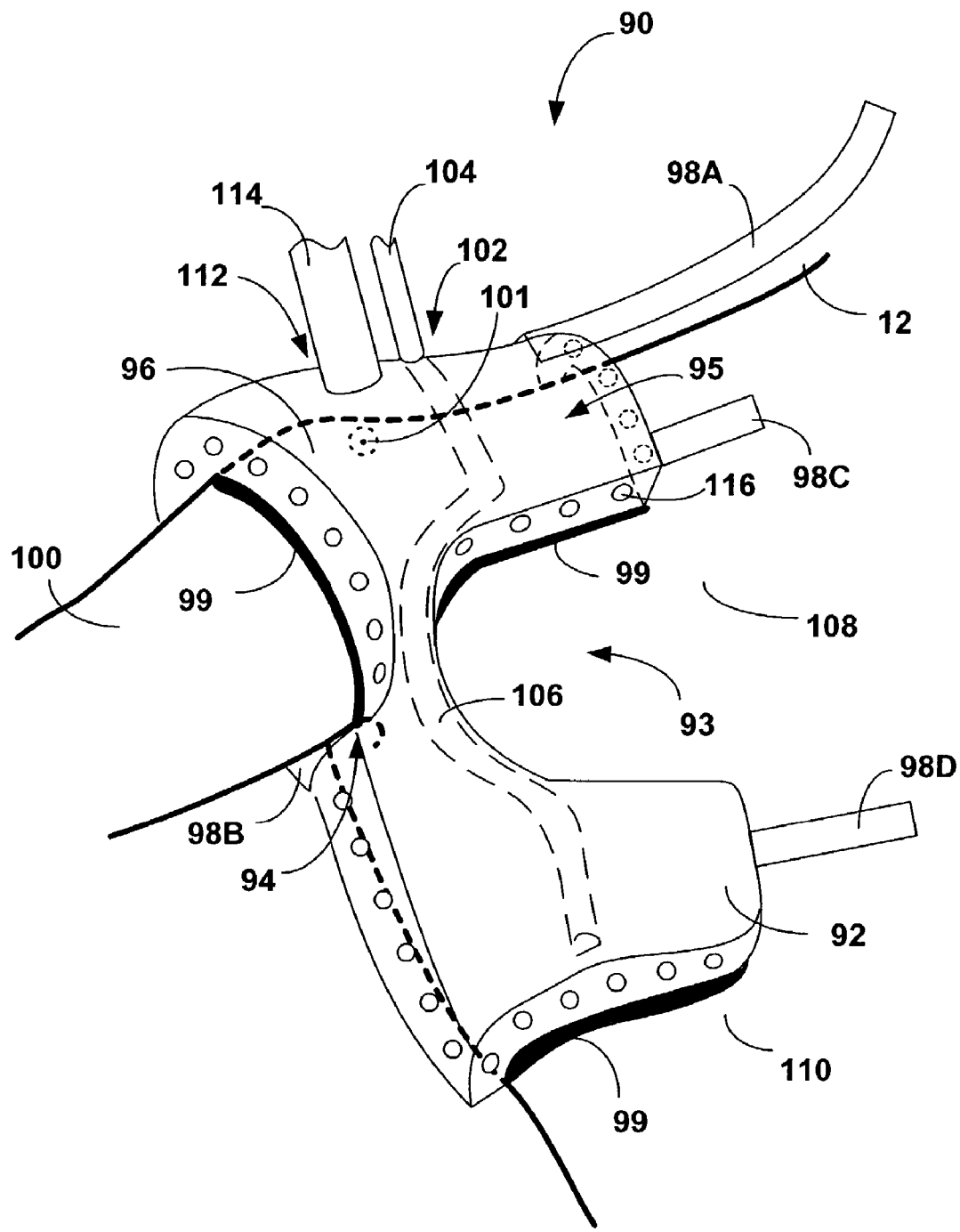
FIG. 6 is a schematic diagram illustrating a front view of an exemplary upper body gear used for cooling of a patient, according to an embodiment of the invention.

FIG. 6 is a schematic diagram illustrating a front view of an exemplary upper body gear 90 used for cooling of a patient 12. Upper body gear 90 is another embodiment of a cooling garment. Upper body gear 90 comprises a shell 92 that surrounds at least a portion of an armpit of patient 12. Shell 92 may also surround a portion of a shoulder of patient 12. Shell 92 may contain a body access 93 to allow access to or accommodate the body of patient 12. For example, body access 93 includes a U-shaped recess. The U-shaped recess may serve several functions. For example, the recess may accommodate the anatomy of a female patient. Second, the recess may allow a medical care provider to have access to the chest of the patient for purposes such as auscultation or defibrillation.

Shell 92 includes a spacer (not shown) that separates at least a portion of upper body gear 90 from the body of patient 12 defining an "upper body space" 95. Fasteners 98A–98D (collectively fasteners 98) secure shell 92 to the body of patient 12. Although in the example of FIG. 6 four fasteners secure shell 92 to patient 12, more or fewer fasteners may secure upper body gear 90.

Fasteners 98 adjust to fit upper body gear 90 on bodies of varying shapes and sizes. Fastener 98A may fasten upper body gear 90 from shoulder 96 to neck area 40 of headgear 10. Fastener 98A may keep upper body gear 90 from sliding down arm 100 of patient 12. Fastener 98B may tighten upper body gear 90 around armpit 94 of patient 12. Fastener 98B may bring upper body gear 90 in closer contact with armpit 94 in order to increase the efficiency of the cooling process. Fasteners 98C and 98D may stretch across the chest of patient 12 and couple to an upper body gear that surrounds the armpit area on the other side of the body of patient 12. Fasteners 98 draw one or more sealing members 99 in contact with the body of patient 12, substantially isolating upper body space 95 created by the spacer inside of body gear 90 from an external environment. Fasteners 98 may be any sort of fastening device such as a zipper, a hook and loop fastener such as VELCRO, an adhesive, a button, a clip, a strap, a buckle or the like. Shell 92 may be constructed of a flexible material that may conform to the shape of the body of patient 12. Shell 92 may further be constructed of an outer material and an inner material. Outer material of shell 92 may be material such as canvas or the like. Inner material of shell 92 may be material such as vinyl liner or the like.

The spacers of upper body gear 90 may include at least one sensor 101 and a communication link (not shown). Sensor 101 generates a signal as a function of a patient parameter such as temperature, oxygen saturation levels, blood flow, heart rate or the like. The communication link may relay the signal to a processor for processing. Sensor 101 and the communication link may be housed in the spacer, in the same fashion as in headgear 10B of FIG. 2. Upper body gear 90 may further comprise a housing (not shown) to house the processor. Alternatively, the processor may also be external to upper body gear 90. Upper body gear 90 may relay the signal obtained by sensor 101 in upper body gear 90 to the same processor as the signal from sensor 54 of headgear 10. Alternatively, upper body gear 90 may relay the signal obtained by sensor 101 of upper body gear 90 to a separate processor as signals from sensor 54 of headgear 10. Sensor 101 may be any of several sensor devices such as a temperature sensor, a thermocouple, an oxygen sensor, a velocity Doppler probe, an electrocardiogram (ECG) sensor, or the like. The communication link may include an optic fiber link, a wireless link, wire link, or the like.

Upper body gear 90 further includes a coolant port 102 that receives a coolant supply 104. Coolant port 102 brings coolant supply 104 into fluid communication with a coolant delivery conduit 106. Coolant delivery conduit 106 of FIG. 5 runs from coolant port 102 to the upper chest 108, around the U-shaped portion encompassing the chest 108, and down to the upper abdominal area 110. Coolant delivery conduit 106, however, is not restricted to the path described. Coolant delivery conduit 106 may follow any sort of path within upper body gear 90. For example, coolant delivery conduit 106 may branch within upper body gear 90. Coolant delivery conduit 106 and coolant supply 104 conform substantially to coolant delivery conduit 38 and coolant supply 36 of headgear 10.

Small apertures in coolant delivery conduit 106 may allow the coolant to drip out, seep out, mist out, spray out, or otherwise exit the lumen of coolant delivery conduit 106. The coolant exits from coolant delivery conduit 106, and an absorbent layer in contact with the body of patient 12 may absorb the coolant. Heat drawn from the direct contact of the coolant and patient 12 may cause the coolant to change from a liquid state to a gaseous state.

Upper body gear 90 further includes a carrier gas port 112 that receives a carrier gas supply 114. Carrier gas port 112 brings carrier gas supply 114 into fluid communication with upper body space 95. Carrier gas supply 114 may include a coupling (not shown) that mates to carrier gas port 112. Carrier gas supply 114 may be constructed of tube-like structures made of materials such as rubber, plastic, or the like.

Carrier gas from carrier gas supply 114 enters upper body space 95 of upper body gear 90 via gas port 112. A carrier gas mover (not shown) may cause the carrier gas to circulate within upper body space 95. Carrier gas mover may be a fan, a pressurized gas source, a pump or the like. The carrier gas circulating within upper body space 95 carries the evaporated coolant out of upper body gear 90 via one or more exit ports 116.

The example described above is a body gear that covers a single armpit. Another upper body gear 90 may be placed on the other armpit of patient 12. The invention also encompasses other arrangements of upper body gear such as a single upper body gear that covers both armpits, an upper body gear without U-shaped chest section, an upper body gear that expands across the back, an upper body gear that extends further down the arm, or the like. Upper body gear 90 may further include multiple coolant delivery conduits, multiple carrier gas intake ports, or both to allow for localized cooling of portions of the body of patient 12.

Upper body gear 90 may include a warm air supply and a warm air nozzle (not shown) to blow warm air on the hand of patient 12. Warm air may reduce shivering, shivering being counterproductive to the cooling process.

Figure 7:
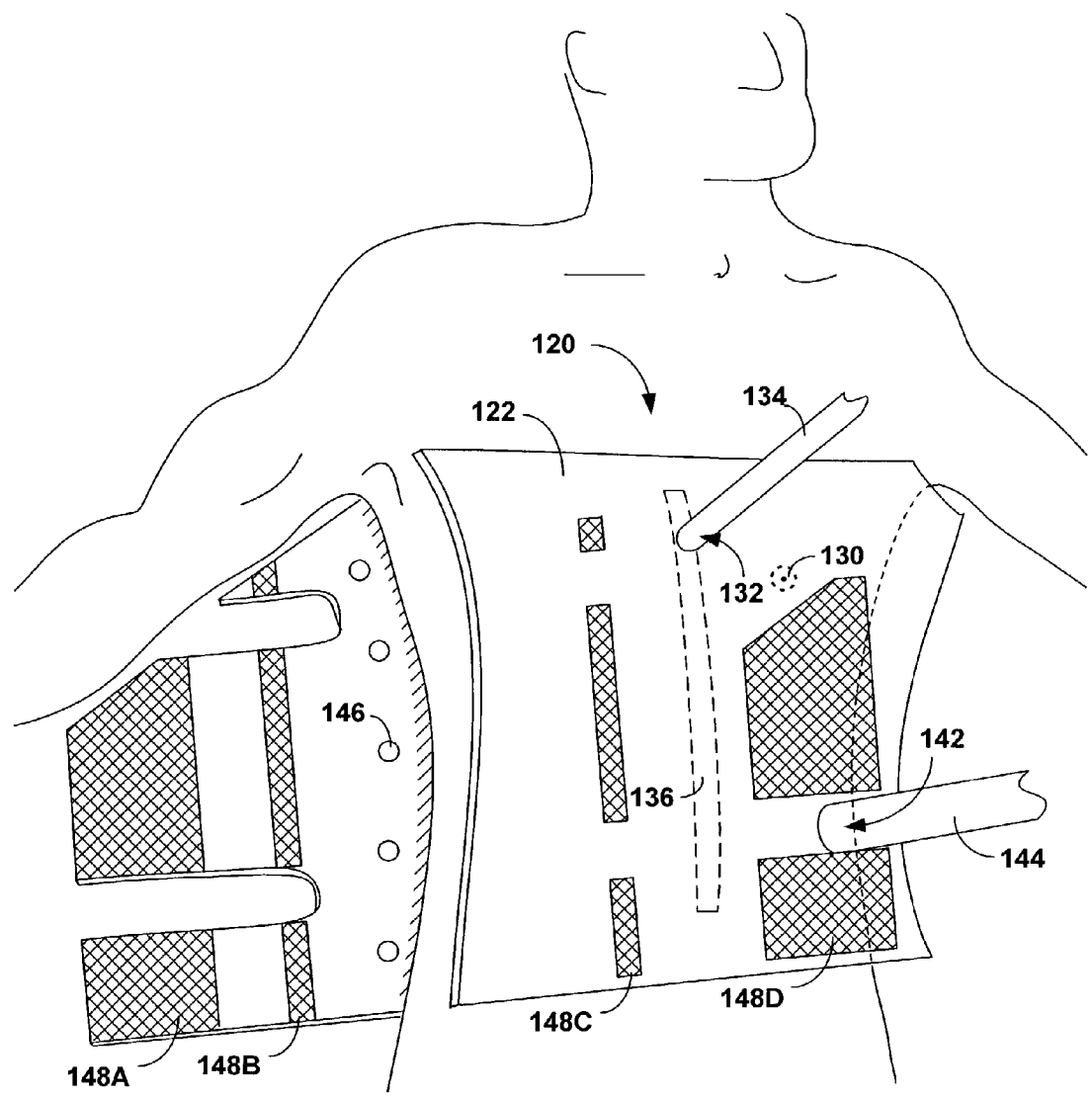
FIG. 7 is a schematic diagram illustrating a front view of another exemplary upper body gear used for cooling of a patient, according to an embodiment of the invention.

FIG. 7 is a schematic diagram illustrating a front view of another exemplary upper body gear 120 used for cooling of patient 12. Body gear 120 is another embodiment of a cooling garment. Upper body gear 120 may cool the body instead of upper body gear 90. Upper body gear 120 comprises a shell 122 that surrounds at least a portion of the torso of patient 12. Shell 122 includes a spacer (not shown) that separates at least a portion of body gear 120 from the body of patient 12 defining a "torso space" 141. Fasteners 148A–148D (collectively fasteners 148) secure shell 122 of upper body gear 120 to the body of patient 12. In the example of FIG. 7, fasteners 148 are hook and loop, e.g., VELCRO, fasteners that secure upper body gear 120 to the torso of patient 12 in an adjustable manner. For example, fasteners 148A and 148B fasten to fasteners 148C and 148D to secure upper body gear 120 to the torso of patient 12. Fasteners 148 need not be hook and loop fasteners. For example, fasteners 148 may be buttons, clips, zippers, straps, buckles or the like. Securing fasteners 148 draws a sealing member (not shown) in contact with the body of patient 12, substantially isolating torso space 141 created by the spacer inside of body gear 120 from an external environment. Shell 122 may be constructed of a flexible material that may conform to the shape of the body of patient 12, and may further be constructed of an outer material and an inner material. Shell 122 may further include a body access (not shown) that allows access to or accommodates the body of patient 12. For example, shell 122 may include a body access (not shown) to accommodate the anatomy of a female patient, to allow medics to perform defibrillation, or the like.

Upper body gear 120 may include at least one sensor 130 and a communication link (not shown). Sensor 130 obtains a signal of some variable of patient 12 and the communication link may relay the signal to a processor for processing. Upper body gear 120 may further comprise a housing (not shown) to house the processor. Alternatively, the processor may also be external to upper body gear 120.

Upper body gear 120 further includes a coolant port 132 that receives a coolant supply 134. Coolant port 132 brings coolant supply 134 into fluid communication with a coolant delivery conduit 136. Coolant delivery conduit 136 runs from the chest of patient 12 to the abdomen of patient 12. Coolant delivery conduit 136, however, is not restricted to the path described. Coolant delivery conduit 136 may follow any sort of path within upper body gear 120. Coolant delivery conduit 136 may further be shaped to expand and contract to accommodate bodies of different sizes and shapes. Coolant supply 134 and coolant delivery conduit 136 conform substantially to coolant supply 36 and coolant delivery conduit 38 of headgear 10.

Small apertures in coolant delivery conduit 136 may allow the coolant to drip out, seep out, mist out, spray out, or otherwise exit the lumen of coolant delivery conduit 136. The coolant exits from coolant delivery conduit 136, and an absorbent layer (not shown) in contact with the body of patient 12 may absorb the coolant. Heat drawn from the direct contact of the coolant and patient 12 may cause the coolant to change from a liquid state to a gaseous state, i.e., to evaporate.

Upper body gear 120 further includes a carrier gas port 142 that receives a carrier gas supply 144. Carrier gas port 142 brings carrier gas supply 144 into fluid communication with torso space 141. Carrier gas supply 144 may include a coupling (not shown) that mates to carrier gas port 142. Carrier gas from carrier gas supply 144 enters torso space 141 of upper body gear 120 via carrier gas port 142. A carrier gas mover (not shown) may cause the carrier gas to circulate within torso space 141. Carrier gas mover may be a fan, a pressurized gas source, a pump or the like. The carrier gas circulating within torso space 141 carries the evaporated coolant out of upper body gear 120 via one or more of exit ports 146.

Upper body gear 120, like upper body gear 90, may allow for localized cooling of portions of the torso. Localized cooling may be accomplished using multiple coolant delivery conduits, multiple carrier gas intake ports, or both.

Figure 8:
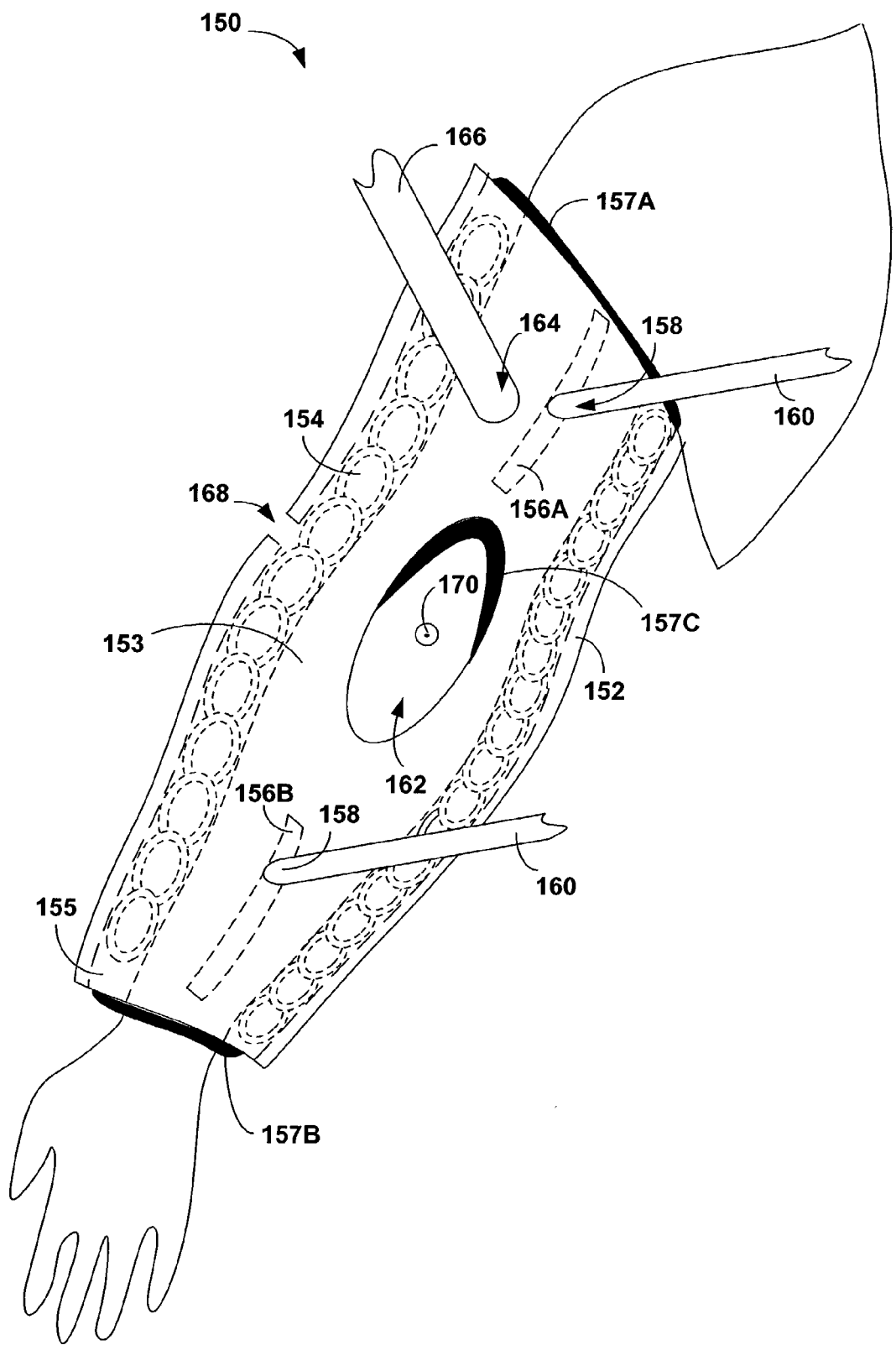
FIG. 8 is a schematic diagram illustrating a front view of another exemplary upper body gear used for cooling of a patient, according to an embodiment of the invention.

FIG. 8 is a schematic diagram illustrating a front view of another exemplary upper body gear 150 that is used to cool patient 12. Upper body gear 150 is another embodiment of a cooling garment. Upper body gear 150 may be used in conjunction with upper body gear 90 or upper body gear 120 to cool patient 12. Alternatively, upper body gear 150 may be used alone to cool patient 12. Upper body gear 150 includes a shell 152 that surrounds at least a portion of an arm 153 of patient 12. Shell 152 includes a spacer that separates at least a portion of shell 152 from arm 153 of patient 12 to create an "arm space" 155.

In the example of FIG 8, a chain spacer 154 separates shell 152 from arm 153 of patient 12. Chain spacer 154 may be made of a lightweight material such as rubber or plastic. Chain spacer 154 need not be strong enough to bear heavy loads in compression or tension, because chain spacer 154 principally acts to create arm space 155, rather than to bear a load. The invention is not limited to use of chain spacer 154, however, and any spacer that separates at least a portion of shell 152 from the body of the patient, including an air spacer, may supplant or cooperate with chain spacer 154 to create the arm space 155. Shell 152 may be constructed of a flexible material that may conform to the shape of the body of patient 12, and may further be constructed of an outer material and an inner material.

Upper body gear 150 may further include a fastener (not shown), such as a snap or a hook and loop, e.g., VELCRO, closure, which secures upper body gear 150 to the body of patient 12, and maybe adjusted. Securing upper body gear 150 to patient 12 via the fasteners draws sealing members 157A–157C (collectively seal members 157) into contact with the body of patient 12. Sealing members 157 substantially isolate arm space 155 created by the spacers, such as chain spacer 154, from an external environment.

Upper body gear 150 may further include coolant delivery conduits 156A and 156B (collectively coolant delivery conduits 156) that deliver coolant to the body in arm space 155 between shell 152 and arm 153. In the example of FIG 8, coolant delivery conduit 156A extends from the upper bicep of arm 53 to the lower bicep of patient 12, and delivers coolant to those portions of the body of patient 12. Coolant delivery conduit 156B extends across the lower portion of arm 53 of patient 12, and delivers coolant to those portions of the body of patient 12. In another embodiment, a single coolant delivery conduit may deliver coolant to the body within arm space 155. Upper body gear 150 may include coolant ports 158 that bring coolant delivery conduits 156 into fluid communication with coolant supplies 160. Small apertures in coolant delivery conduits 156 may allow the coolant to drip out, seep out, mist out, spray out, or otherwise exit the lumen of coolant delivery conduits 156. The coolant exits from coolant delivery conduit 156, and an absorbent layer (not shown) in contact with the body of patient 12 may absorb the coolant. Heat drawn from the direct contact of the coolant and patient 12 may cause the coolant to change from a liquid state to a gaseous state.

Between coolant delivery conduits 156 may be a body access 162 that allows access to a portion of the body for treatments such as intravenous drips or injections. Upper body gear 150 may include more than one body access. Another seal member 157C may be located around body access 162, to prevent leaking of coolant, carrier gas, or the like.

Upper body gear 150 further includes a carrier gas port 164 that receives a carrier gas supply 166. Carrier gas port 164 brings carrier gas supply 166 into fluid communication with arm space 155. Carrier gas from carrier gas supply 166 enters arm space 155 of upper body gear 150 via carrier gas port 164. A carrier gas mover (not shown) may cause the carrier gas to circulate within arm space 155. The carrier gas circulating within arm space 155 carries the evaporated coolant out of upper body gear 150 via one or more of exit ports 168.

Upper body gear 150 may allow for localized cooling of portions of arm 153 of patient 12 using multiple coolant delivery conduits 156, multiple carrier gas intake ports 158, or both.

Upper body gear 150 may also include at least one sensor 170 for generating a signal as a function of a patient parameter such as temperature, oxygen saturation levels, blood flow, heart rate or the like. Spacers 154 may include sensor 54. Upper body gear 150 may also include a communication link (not shown) that relays the signal from sensor 170 to a processor for processing. Upper body gear 150 may further comprise a housing (not shown) to house the processor. However, the processor may be external to upper body gear 150.

Upper body gear 150 may include a warm air supply and a warm air nozzle (not shown) to blow warm air on the hand of patient 12. Warm air may reduce shivering, shivering being counterproductive to the cooling process.

Upper body gear 150 may be constructed in two separate pieces to accommodate the placement a non-invasive blood pressure (NIBP) cuff on patient 12. A first piece may cover the upper portion of the arm and a second piece may cover the lower portion of the arm. Alternatively, the non-invasive blood pressure cuff may be included in the construction of a single piece upper body gear 150. Further, a separate upper body gear 150 may be placed on each arm of patient 12.

Figure 9:
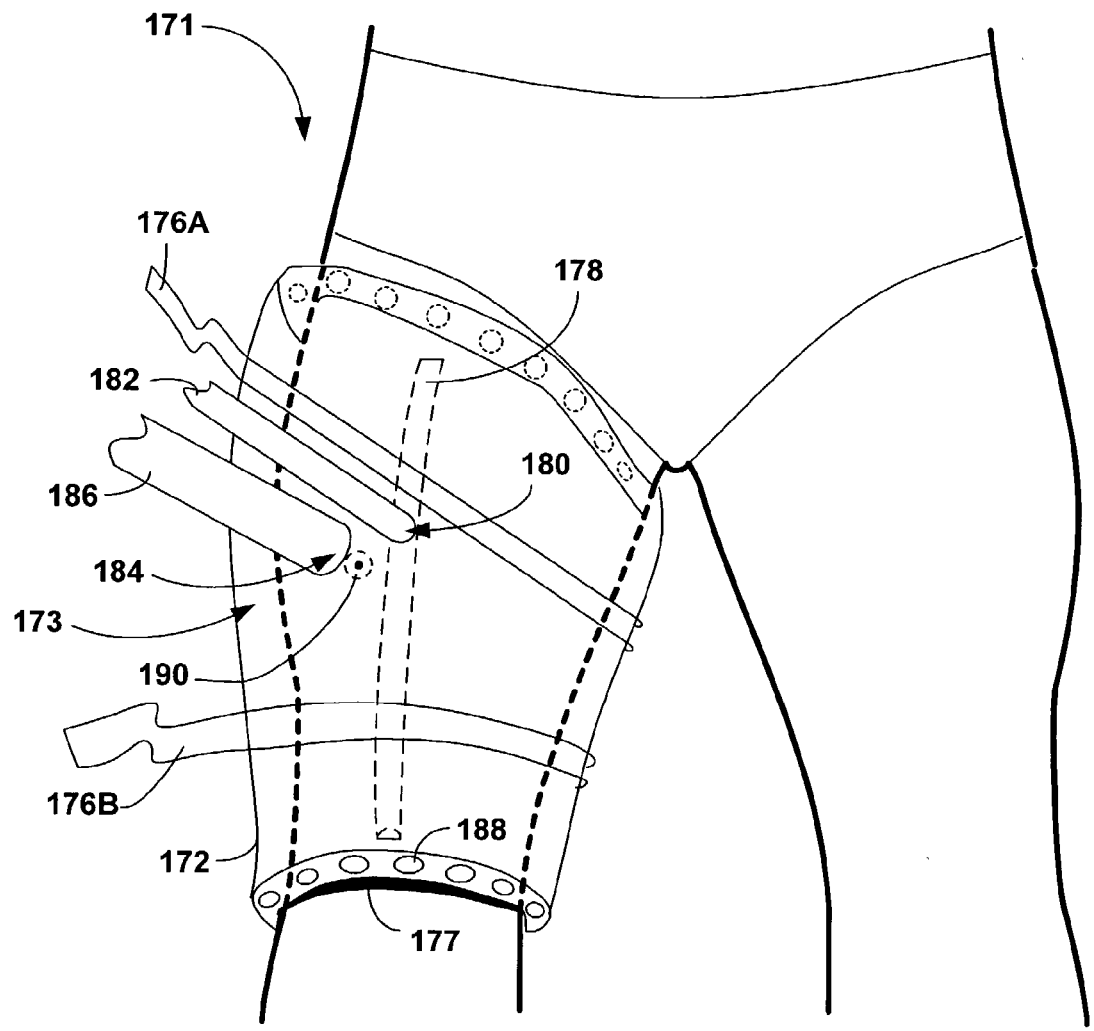
FIG. 9 is a schematic diagram illustrating a front view of an exemplary lower body gear used for cooling of a patient, according to an embodiment of the invention.

FIG. 9 is a schematic diagram illustrating a front view of an exemplary lower body gear 171 used for cooling of a patient 12. Lower body gear 171 is yet another embodiment of a cooling garment. Lower body gear 171 includes a shell 172 that surrounds at least a portion of a thigh/groin area of patient 12. Shell 172 may include spacers (not shown) that separate at least a portion of the lower body gear from the body of patient 12 defining a "lower body space" 173. Lower body gear 171 may further include fasteners 176A and 176B (collectively fasteners 176) that secure shell 172 to the body of patient 12. Fasteners 176 adjust to fit lower body gear 171 on bodies of varying shapes and sizes. For example, fastener 176A may secure lower body gear 171 about the upper thigh region, while fastener 176B may secure lower body gear 171 about the lower thigh and kneecap region. Fasteners 176 may draw a sealing member 177 in contact the body of patient 12, substantially isolating lower body space 173 created by the spacers from an external environment. Shell 172 may further include a body access (not shown) that allows access to or accommodates the body of patient 12. Shell 172 may be constructed of a flexible material that may conform to the shape of the body of patient 12, and may further be constructed of an outer material and an inner material.

Lower body gear 171 further includes a coolant delivery conduit 178 that delivers coolant to the body in lower body space 173. In the example of FIG. 9, coolant delivery conduit 178 extends from the upper thigh and groin region to the lower thigh and kneecap region. However, coolant delivery conduit may follow any sort of path within lower body gear 171. Lower body gear 171 may also include a coolant port 180 that may bring coolant delivery conduit 178 into fluid communication with a coolant supply 182. Small apertures in coolant delivery conduits 178 may allow the coolant to drip out, seep out, mist out, spray out, or otherwise exit the lumen of coolant delivery conduits 178. The coolant exits from coolant delivery conduit 178, and an absorbent layer (not shown) in contact with the body of patient 12 may absorb the coolant. Heat drawn from the direct contact of the coolant and patient 12 may cause the coolant to change from a liquid state to a gaseous state.

Lower body gear 171 further includes a carrier gas port 184 that receives a carrier gas supply 186. Carrier gas port 184 brings carrier gas supply 186 into fluid communication with lower body space 173 created by the spacers. Carrier gas supply 186 may include a coupling (not shown in FIG. 9) that mates to carrier gas port 184. Carrier gas from carrier gas supply 186 enters lower body space 173 of lower body gear 171 via carrier gas port 184. A carrier gas mover (not shown) may circulate the carrier gas within lower body space 173. The carrier gas carries the evaporated coolant out of lower body space 173 through one or more exit ports 188.

Lower body gear 171 may include at least one sensor 190 and a communication link (not shown). Sensor 190 generates a signal as a function of a patient parameter. The communication link may relay the signal to a processor for processing. The process may be internal or external to lower body gear 171. Sensor 190 may be housed within the spacers that create lower body space 173.

The example of FIG. 9 described above is a body gear that covers a single thigh and groin area. Another lower body gear 171 may be placed on the other thigh of patient 12. The invention, however, encompasses a lower body gear may be in a single thigh or groin piece. The invention further encompasses a lower body gear that may extend farther down the leg than the knee. For example, lower body gear 171 may extend to the shin or even all the way to the feet of patient 12. Lower body gear may further allow for localized cooling of the lower body of patient 12 using multiple coolant delivery conduits, multiple carrier gas intake ports, or both.

Upper body gear 150 may include a warm air supply and a warm air nozzle (not shown) to blow warm air on the feet of patient 12. Warm air may reduce shivering, shivering being counterproductive to the cooling process.

Figure 10:
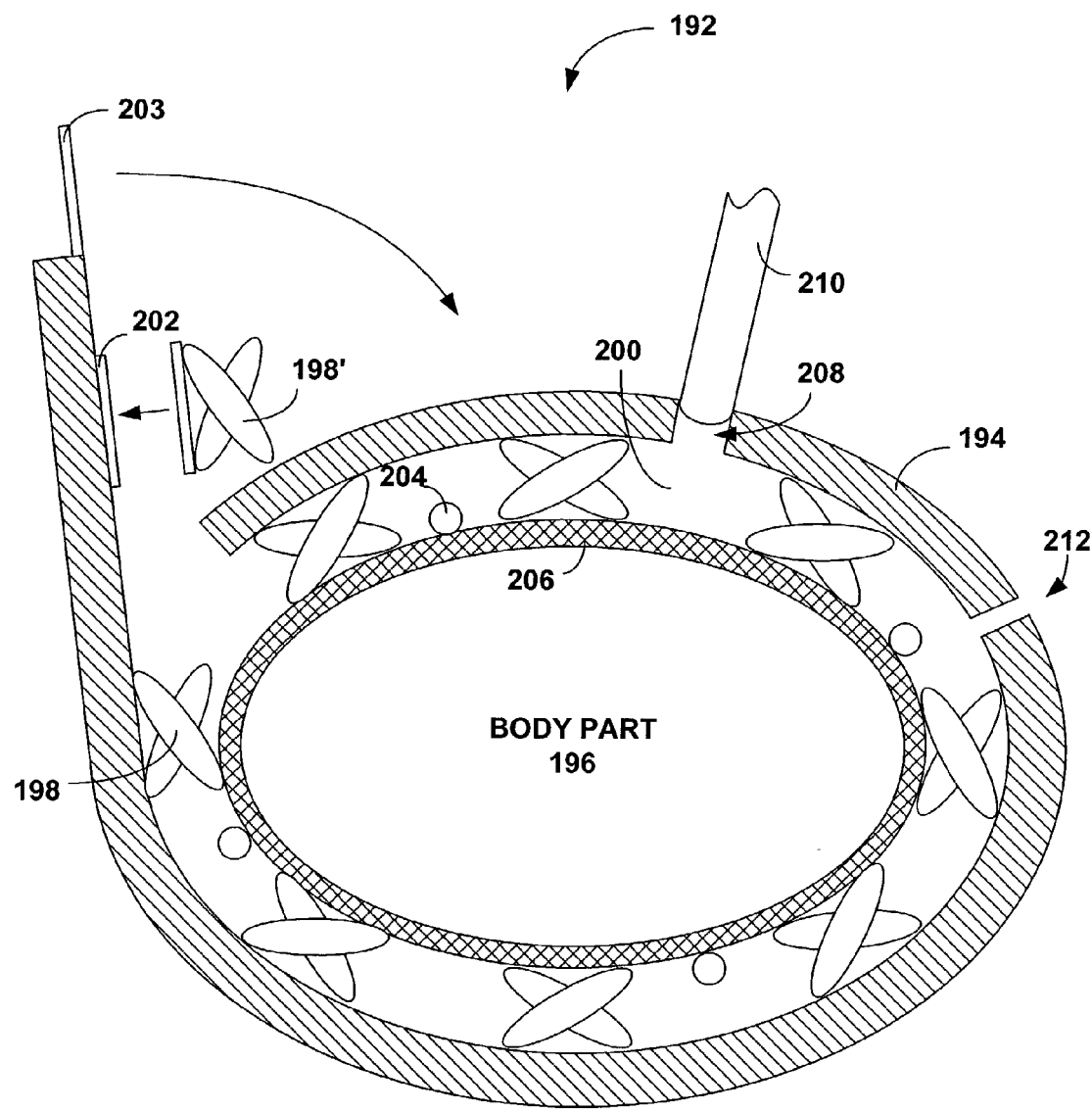
FIG. 10 is a schematic diagram illustrating a cross-sectional view of a body gear, according to an embodiment of the invention.

FIG. 10 is a schematic diagram illustrating a cross-sectional view of a body gear 192. Body gear 192 may represent any of upper body gears 90, 120, and 150 or lower body gear 171. Body gear 192 includes a shell 194 that surrounds a body part 196 of a patient 12. Shell 194 includes spacers 198, such as chain spacers, air spacers or the like that separate at least a portion of shell 194 from body part 196 creating a space 200. Some or all of spacers 198, such as spacer 198', may be attachable to and detachable from shell 194. For instance, when body gear 192 must be used fir a larger body size, additional spacers 198' may be attached to attachment points 202. Attachment points 202 may be sites that include attachment mechanisms such as hook and loop fasteners, e.g., VELCRO, adhesive or clasps. When spacers 198' are not attached to attachment points 202, the attachment point 202 may be a fastener used to secure body gear 192 to patient 12. Body gear 192 may further include a permanent fastener 203, such as a strap, that secures body gear 192 on body part 196 regardless of whether all attachment points 202 are occupied by spacer 198'.

Body gear 192 further includes one or more coolant delivery conduits 204 that deliver coolant to body part 196. Each of coolant delivery conduits 204 may be a separate coolant delivery conduit. Alternatively, each of coolant delivery conduits 204 may be a branch from a single coolant delivery conduit that follows a path within body gear 192. Coolant delivery conduit 204 may have small apertures that allow the coolant to drip out, seep out, mist out, spray out, or otherwise exit the lumen of coolant delivery conduits 204. An absorbing layer 206 may absorb the coolant that exits coolant delivery conduits 204. Absorbing layer 206 keeps the coolant in contact with body part 196 of patient 12. Heat drawn from the direct contact of the coolant and patient 12 may cause the coolant to change from a liquid state to a gaseous state.

Body gear 192 further includes a carrier gas intake port 208 that fluidly connects space 200 to a carrier gas supply 210. Carrier gas enters space 200 via carrier gas intake port 208, and circulates within space 200. The carrier gas carries the evaporated coolant from space 200 via an exit port 212.

The cooling process occurring inside of the body gear 192 is similar to that of headgear 10 described above. Space 200 within body gear 192 receives a carrier gas from carrier gas supply 210 via carrier gas port 208. Coolant delivery conduit 204 receives a coolant from a coolant supply via a coolant port.

A carrier gas mover circulates the carrier gas within space 200 of body gear 192. The liquid coolant exits the lumen of coolant conduit 204 via small apertures in coolant conduit 204. The coolant contacts the body of patient 12. The coolant may contact the body in absorbent layer 206 or may be applied directly to the body of patient 12. Heat from the body causes the coolant to evaporate. The evaporation and convection heat transfer processes cool patient 12.

The circulating carrier gas encounters evaporated coolant in space 200, and carries the coolant in gaseous form away from patient 12. The carrier gas and gaseous coolant are discharged out exit port 212 and fresh carrier gas and coolant replace what has been discharged.

Figure 11:
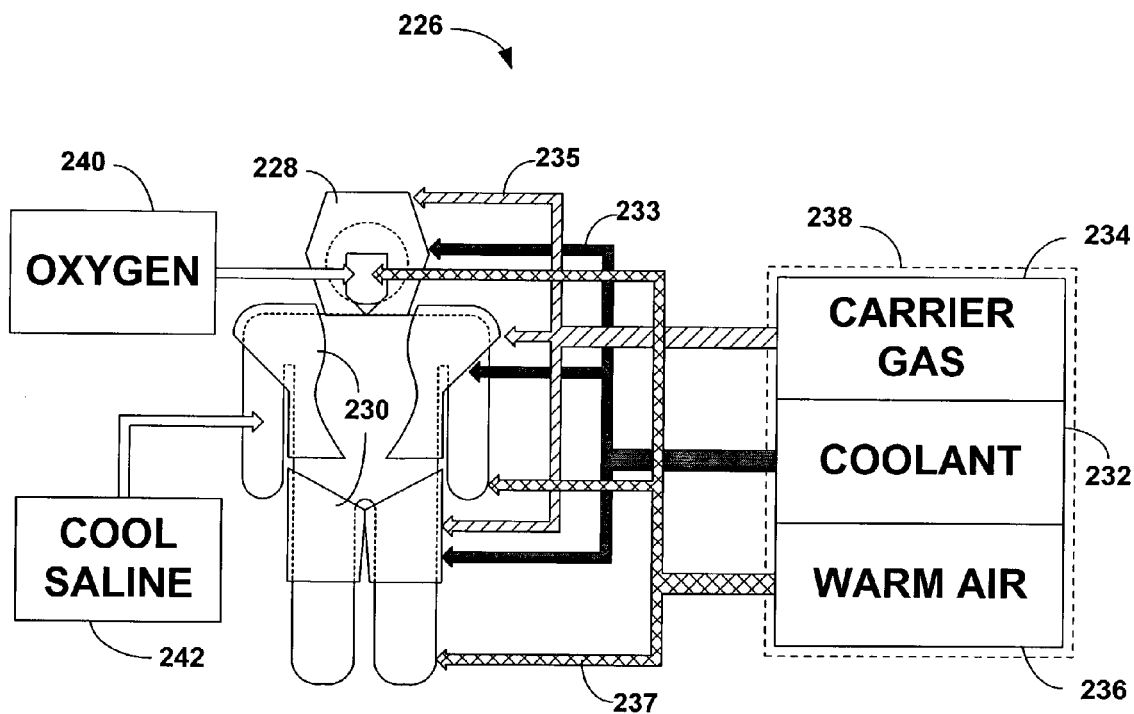
FIG. 11 is a schematic diagram illustrating a cooling system used to cool a patient, according to an embodiment of the invention.

FIG. 11 is a schematic diagram illustrating a cooling system 226 in which multiple cooling garments are used to cool a patient 12. Cooling system 226 may be applied to patient 12 after patient 12 suffers some kind of traumatic event such as stroke, cardiac arrest, head trauma or the like. Cooling system 226 may include a headgear 228, which covers at least a portion of the head of patient 12. Headgear 228 may be headgear 10A described in FIGS. 1-3, headgear 10B described in FIG. 5, or any other sort of headgear consistent with the principles of the invention.

Cooling system 226 may also include a body gear 230 that covers at least a portion of the body of patient 12. Body gear 230 may include any combination of upper body gear 90, upper body gear 120, upper body gear 150, lower body gear 171, or any other type of body gear consistent with the principles of the invention.

Both headgear 228 and body gear 230 may be constructed of materials that are sterilizable and, consequently, reusable. All or only a portion of headgear 228 and body gear 230 may be reusable. For example, an absorbent layer within headgear 228 may be replaced after every use, while all other portions of headgear 228 and body gear 230 may be sterilized and reused. Headgear 228 and body gear 230 may be sterilized using an autoclave, steam, liquid, or any other sterilization method.

Cooling system 226 may further include a coolant supply container 232. Coolant supply container 232 supplies coolant to both headgear 228 and body gear 230 via coolant supply 233. Alternatively, a separate coolant supply may supply coolant to the separate cooling pieces of cooling system 226. The coolant supplied to cooling system 226 is typically a liquid coolant such as water, alcohol, or a mixture of water and alcohol. Alternatives, however, may be used. The liquid coolant may be cooled before entering headgear 228 and body gear 230.

Cooling system 226 further includes a carrier gas supply container 234 that supplies carrier gas to both headgear 228 and body gear 230 via carrier gas supply 235. Alternatively, a separate carrier gas supply container may supply carrier gas to the separate cooling pieces of cooling system 226. Typical carrier gases include carbon dioxide, nitrogen, air, or any combination thereof. Typically, carbon dioxide and nitrogen would be stored in liquid form and expanded to a gas so as to minimize space and cool the gas supplied to headgear 228 and/or body gear 230. One or more expansion valves may be interposed between the carrier gas supply 235 and the cooling garments. Expansion valves may regulate the amount of liquid carbon dioxide or nitrogen expanded to a gas. The expansion valves may be proximate to carrier gas supply 235, or proximate to the garments so as to minimize the temperature loss as the gas flows to the cooling garments. A cooling garment may include an expansion valve. An expansion valve may be, for example, coupled to a carrier gas port of a garment.

Further, the expanded carbon dioxide or nitrogen may be mixed with air in order to adjust the temperature to a safe range for application to patient 12. The carrier gas may also be cooled by a cooling canister, such as a blue ice canister or by a heat exchanger before being supplied to cooling devices of cooling system 226. The carrier gas may further be dehumidified before entering headgear 228 and body gear 230 in order to absorb more water vapor and, in turn, enhancing the evaporative cooling process.

Cooling system 226 may also include a warm air supply container 236 to supply warm air to parts of the body not covered by cooling devices via warm air supply 237. For example, warm air supply container 236 may supply warm air to the face, hands, or feet to prevent patient 12 from shivering, which is counterproductive to the cooling process.

A container supply box 238 may include coolant supply 232, carrier gas supply 234, and warm air supply 236. Container supply box 238 may be convenient when the supplies 232, 234, 236 must be administered at the site of a traumatic event.

Cooling system may also include oxygen supply container 240 to supply oxygen to patient 12. The oxygen may be supplied to patient 12 via cannula or mask for therapeutic purposes. In some embodiments of the invention, the carrier gas is carbon dioxide, and carbon dioxide leak from the headgear in the vicinity of patient's face 20. Supplying oxygen to the patient may reduce the quantity of carbon dioxide inhaled by patient 12. Further, the oxygen may be cooled for lockout concerns.

Patient 12 may further be injected with a cool saline from cool saline container 242. For example, an infusion pump may pump cool saline into the body of patient 12 to complement the cooling process. The cool saline injected into the blood stream may increase the efficiency of the cooling process by directly cooling the blood that circulates through the body of patient 12.

Figure 12:
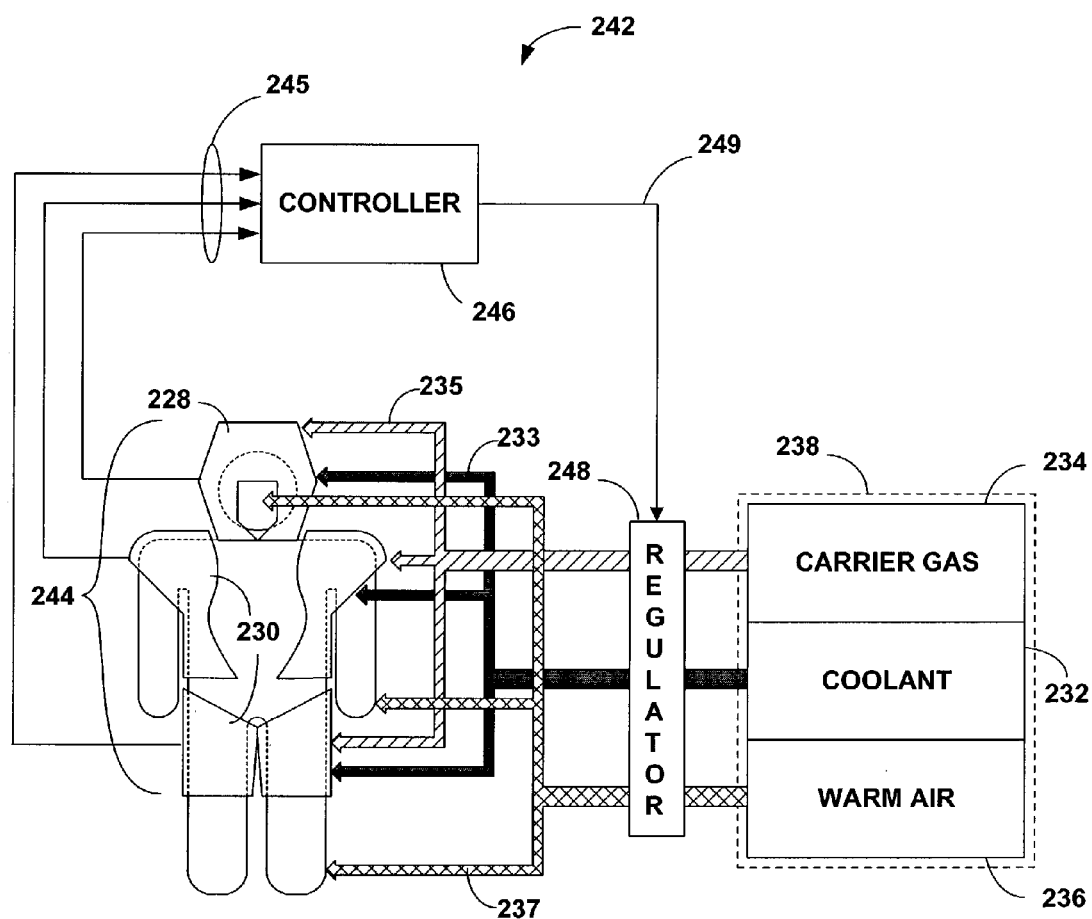
FIG. 12 is a schematic diagram illustrating an exemplary cooling feedback system, according to an embodiment of the invention.

FIG. 12 is a schematic diagram illustrating an exemplary cooling feedback system 242. Cooling feedback system 242 includes a cooling device 244. Cooling device 244 may include multiple cooling garments. Cooling device 244 illustrated in FIG. 12 includes three cooling garments: a headgear 228 and two body gear 230. The cooling garments of cooling device 244 function as described above. Although cooling device 244 of FIG. 12 consists of three cooling garments, the number of cooling garments is not restricted to three. For instance, cooling device 244 may include a single cooling garment or more than one cooling garment. Cooling device 244 also need not be restricted to cooling the head, groin, and armpit areas of patient 12. For example, cooling device 244 may include cooling garments that cover other areas of the body of patient 12, such as a torso, an arm, a leg, or the like.

A coolant supply container 232 and a carrier gas supply container 234 may supply coolant and carrier gas and warm air to headgear 228 and body gear 230 via coolant supply 233 and carrier gas supply 235. In addition, a warm air supply source 236 may provide warm air to areas of the body of patient 12 via warm air supply 237. A container supply box 238 may house the coolant supply container 232, carrier gas supply container 234, warm air supply source 236 as described above.

Each cooling garment may receive the coolant and carrier gas from the same respective supply containers. Alternatively, each cooling garment may receive coolant and carrier gas from separate respective supply containers. In a typical embodiment of the invention, the coolant and carrier gas received by each cooling garment may be individually controlled.

Similarly, a single warm air supply source may provide warm air to several body sites, other sites may be served by individual warm air sources. The warm air supplied to each site may be individually controlled.

Cooling device 244 includes one or more sensors (not shown in FIG. 12) to measure a signal as a function of a patient parameter. The sensor may be in contact with the body within any of the cooling garments. For example, headgear 228 and each of body gear 230 may each include a sensor. Furthermore, there may be more than one sensor in each cooling garment of cooling device 244. The sensors may also be placed outside of the cooling garments. Sensors outside of the cooling garments may be in contact with the body of patient 12. For example, a tympanic temperature sensor may be placed in the ear of patient 12, or temperature sensors may measure oral, rectal or bladder temperatures. Alternatively, sensors outside of the cooling garments may be located within supplies, such as within coolant supply 233, carrier gas supply 235, or warm air supply 237. Sensors may generate signals as a function of a patient parameter such as temperature, oxygen saturation levels, blood flow, heart rate, brain electrical action, end tidal carbon dioxide levels or the like. Furthermore, the sensor may generate a signal as a function of a cooling element parameter such as the temperature of the coolant, temperature of the gas, flow rate of the gas, flow rate of the coolant, and the like.

Cooling device 244 communicates the signals from the sensors of the cooling garments to a controller 246 via a communication bundle 245, a wireless link, or any other communication devices. For example, cooling feedback system 242 may contain a communication bundle 245 that contains one or more communication links extending from cooling device 244. Communication bundle 245 may relay the signals from the sensors of the cooling garments to a controller 246. Communication bundle 245 may communicate the signals directly from the sensors to controller 246. Alternatively, the signals from the sensors may be processed at cooling device 244 before being communicated to controller 246. The communication links within the cooling garments may communicate the signals generated by the sensors to one or more processors within cooling device 244 for processing. The processors in cooling device 244 may, for example, compare the signals to thresholds, filter the signals and convert them from analog signals to digital signals with an analog to digital (A/D) converter. The processors in cooling device 244 may also encode the signals for transmission to controller 246. Encoding the signals may allow the use of smaller communication bundles 245, which are less likely to interfere with the emergency medical personnel, doctors, or other users of cooling feedback system 242. The processor of cooling device 244 may be located within any of the cooling garments of cooling device 244. A single processor may process the signals of all of the cooling garments of cooling device 244. Alternatively, a separate processor housed in each separate cooling garment may process the signals from the sensors of the respective cooling garment.

Controller 246 receives signals from cooling device 244 via communication bundle 245. Controller 246 may include a processor that processes the signals. The processor in controller 246 may perform comparing, filtering and A/D conversion. The processor in controller 246 may further process the signal for display to a user, such as emergency medical personnel, a doctor, or any other user via a display. Controller 246 may receive an ECG signal, for example, and display it to the user via a display.

Controller 246 may receive input from the user, such as a desired value of a patient parameter. For example, controller 246 may receive input from the user indicating a desired core body temperature or range of body temperatures. When controller 246 receives signals from temperature sensors, controller 246 may determine whether cooling device 244 is operating within the desired range by comparing the signals from the temperature sensors to the desired core body temperature input by the user. Controller 246 may compare the signal from each of the temperature sensors to the input core body temperature. Furthermore, the user may input a desired value for other variables such as a minimum heart rate, high and low oxygen saturation levels or the like. Cooling may have an effect upon one or more of these patient parameters, which the sensors may monitor.

When the received signal, or combination of signals, indicates that a patient parameter is outside of a specified range, controller 246 may adjust the delivery of one or more of the coolant, carrier gas, and/or warm air. With an adjustment to the coolant, carrier gas, and/or warm air, cooling device 244 may bring the patient parameter into the appropriate range. Further, controller 246 may sound an alarm to notify the user that cooling device 244 is operating outside an appropriate range.

For instance, a user may program controller 246 to recognize a minimum threshold core body temperature. During cooling, temperature sensors may monitor core body temperature, and one or more processors may compare the measured body temperature to the minimum threshold core body temperature. When core body temperature falls below the programmed minimum, controller 246 may send a regulation signal to a regulator 248 via a feedback link 249. Feedback link 249 may be an optical fiber link, a wireless link, a wire link, or the like. Regulator 248 may receive the regulation signal from controller 246, and adjust the delivery of coolant, carrier gas, and/or warm air in response to the signal. Controller 246 may, for example, send a regulation signal to regulator 248 directing the regulator to reduce the amount of carrier gas supplied to one or more cooling garments. In response to the regulation signal, regulator 248 may adjust a valve or other regulation mechanism to reduce the flow rate of carrier gas to one or more cooling garments. Cooling garments may be individually regulated. Regulator 248 may adjust the carrier gas in ways other than or in addition to flow rate, such as by adjusting the temperature of the carrier gas, adjusting the mixing ratio of the carrier gas, or changing the speed of a fan. Furthermore, regulator 248 may adjust the delivery of coolant or warm air at the same time.

In another example, a user may program controller 246 to recognize different ranges of body temperatures, such as a high range of temperatures and a low range of temperatures. When temperature sensors indicate that the body temperature is in the high range, controller 246 may send a regulation signal to a regulator 248 via a feedback link 249 to pursue an aggressive cooling therapy. For example, cooling feedback system 242 may include a "blast" cooling mode that provides rapid cooling to patients that may benefit from it. The blast cooling mode may cool the body below the frostbite level for a few minutes and then proceed to cool the body more conservatively. The blast cooling may be discontinued before frostbite sets in. Alternatively, when temperature sensors indicate that the body temperature has dropped into the low range, controller 246 may send a regulation signal to a regulator 248 to pursue more moderate cooling therapy instead of maintaining an aggressive cooling therapy for that few minutes. Regulator 248 may adjust the delivery of coolant, carrier gas, and/or warm air in response to the signals from controller 246.

The operation of the invention is not limited to setting a minimum threshold core body temperature or a range of body temperatures, but may involve other patient parameters as well. In addition, feedback system 242 may also control devices that supplement the cooling process of cooling device 244. For example, feedback system 242 may regulate the amount of oxygen supplied to patient 12, the temperature of the cool saline injected into patient 12, or the amount of cool saline injected into patient 12.

Figure 13:
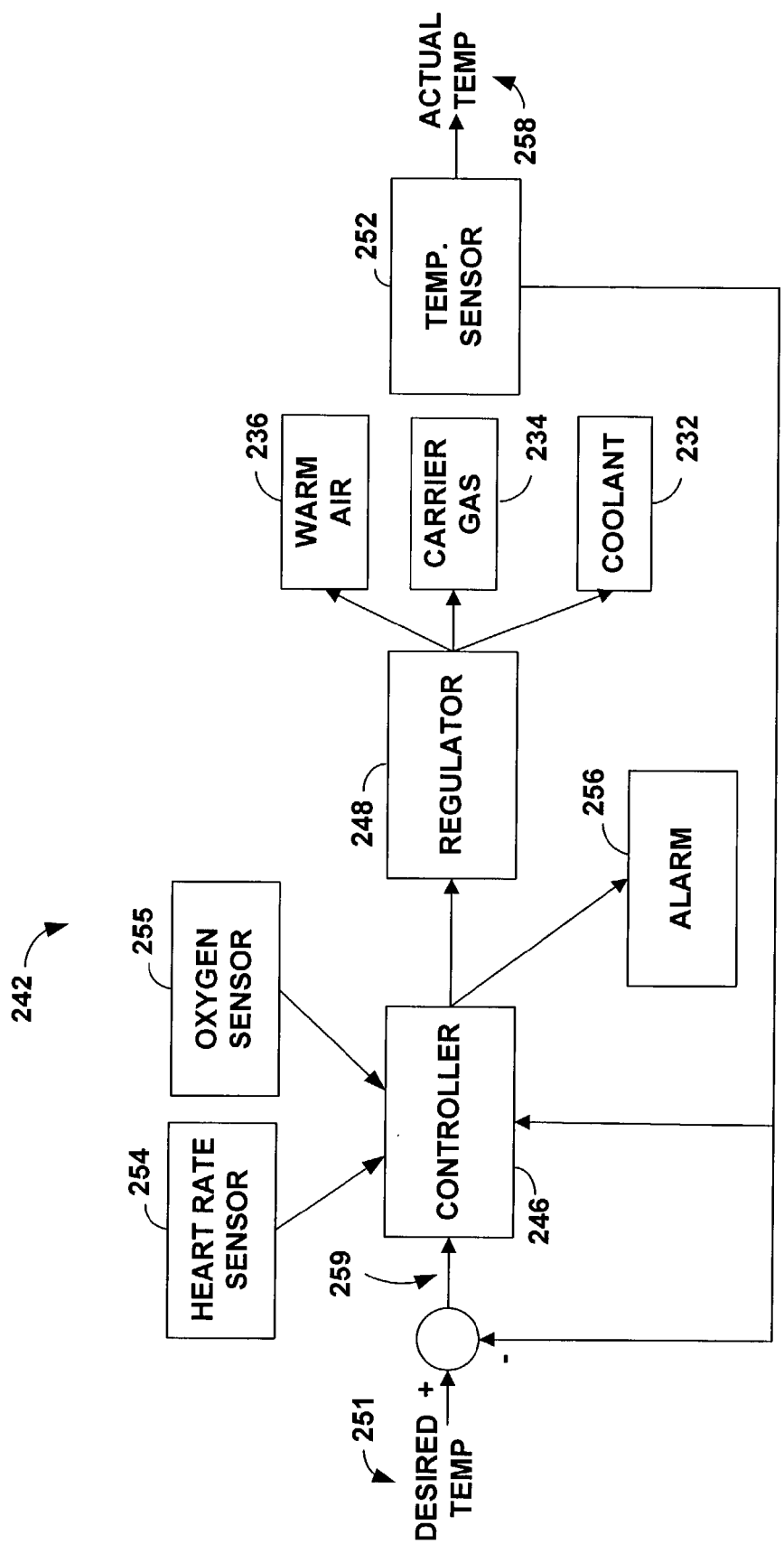
FIG. 13 is a block diagram illustrating the cooling feedback system of FIG. 12.

FIG. 13 is a block diagram illustrating cooling feedback system 242. A user, such as emergency medical personnel or a doctor, may input a desired value for a parameter of patient 12. In the example of FIG. 13, the user may program a desired temperature 251. For purposes of illustration, temperature 251 will be assumed to be a target body temperature. Feedback system 242 may compare desired temperature 251 programmed by the user to a temperature signal generated by a temperature sensor 252. Temperature sensor 252 may measure a temperature such as the core body temperature or the skin temperature of the body. The output signal 258 may be the actual temperature of patient 12 as measured by temperature sensor 252.

Controller 246 receives an error signal 259 as a function of the difference between desired temperature 251 and output temperature 258 measured by temperature sensor 252. Controller 246 may use error signal 259 to determine whether cooling device 244 has produced a body temperature that is at, above, or below the target body temperature. Controller 246 may transmit a regulation signal to regulator 248 based on the determination.

Regulator 248 may adjust one or more of coolant 232, carrier gas 234 and/or warm air 236 in response to the regulation signal. Coolant 232, carrier gas 234 and/or warm air 236 may affect the body temperature of patient 12, which is measured by temperature sensor 252. Regulator 248 may regulate coolant 232, carrier gas 234 and warm air 236 independently by, for example, controlling coolant supply container 232, the carrier gas supply container 234, and warm air supply source 236.

Controller 246 need not rely on error signal 259, and may further receive a signal directly from temperature sensor 252. Controller 246 may transmit a regulation signal to regulator 248 based on the actual temperature as measured by temperature sensor 252.

In addition, controller 246 may receive signals from other sensors such as a heart rate sensor 254, an oxygen sensor 255, or a carbon dioxide sensor. Controller 246 may regulate cooling device 244 as a function of error signal 259 as long as the heart rate and oxygen saturation level are within a safe range. However, if the heart rate or oxygen saturation level of patient 12 were to enter an unsafe range, controller 246 may begin to regulate cooling device 244 in response to the signal received directly from sensor 254 or 255, respectively. Controller 246 may, for example, scale back cooling until the heart range is back in a safe range. In other words, controller 246 may be programmed to judge a safe heart rate or oxygen saturation level as having a higher priority than a desired body temperature. The prioritization scheme may be programmed by the user. Controller 246 may further allow the user to manually turn the cooling system on and off.

When controller 246 receives a signal from a sensor, such as temperature sensor 252, heart rate sensor 254, or oxygen sensor 255, which is outside of an appropriate operating range or otherwise indicates a danger to patient 12, controller 246 may sound an alarm 256 to alert the user. Alarm 256 may have multiple sounds to indicate which variable of patient 12 is outside of the desired operating range. The alarm may also comprise a computer-generated voice. In addition, controller 246 may cause an indication message to appear on the user display concurrently with the sound emitted by alarm 256.

If the heart of patient 12 should suddenly go into ventricular fibrillation, for example, controller 246 may receive a signal from heart rate sensor 254 that the heart is in ventricular fibrillation. Controller may sound an alarm 256 and may display a visual message as well. In these circumstances, restarting the heart may be more important than cooling. Controller 246 may alter or suspend cooling functions in one or more cooling garments until the patient has been returned to a normal sinus rhythm. Further, controller 246 may turn on the cooling when ventricular fibrillation is detected.

Figure 14:
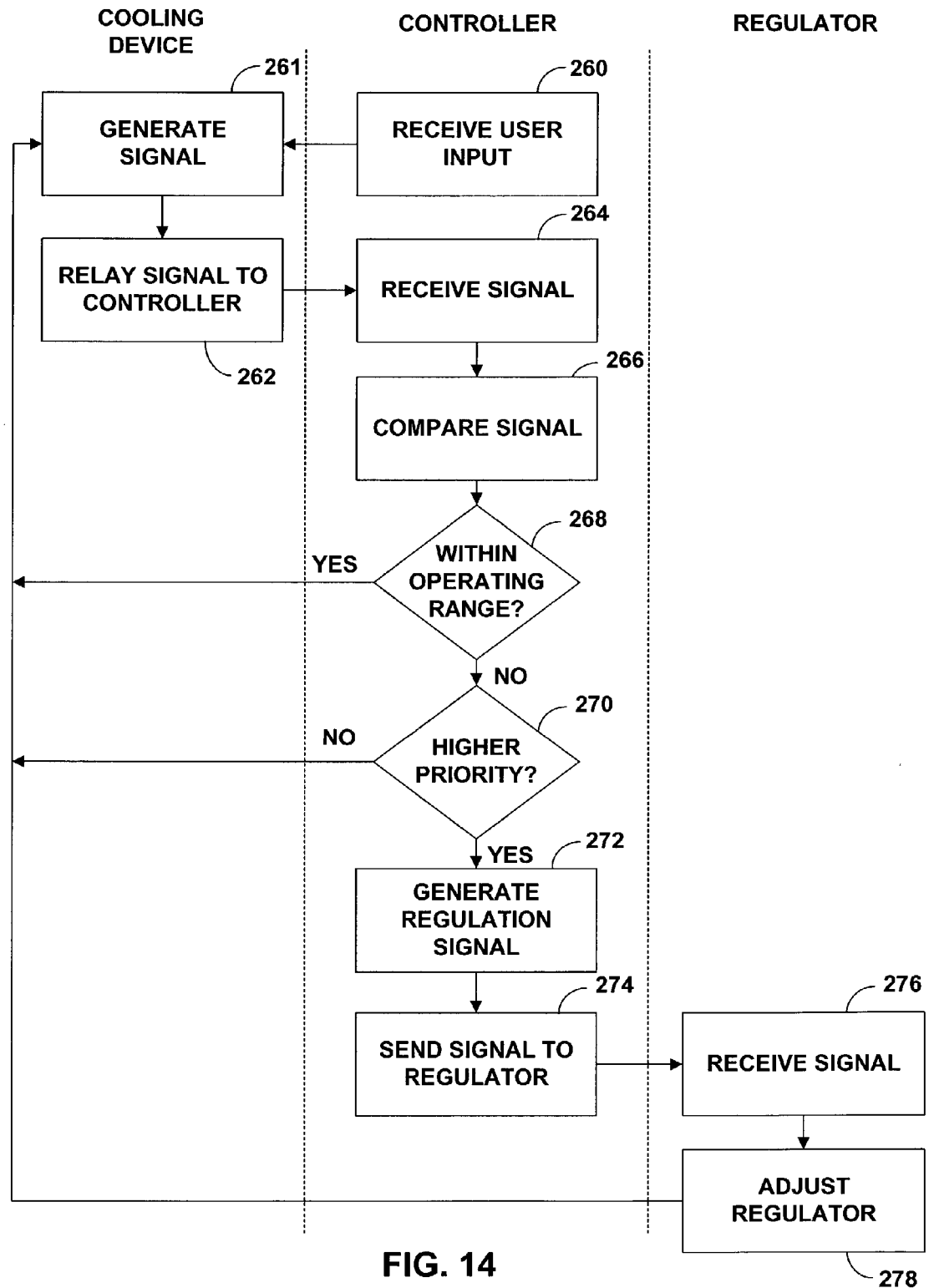
FIG. 14 is a flowchart illustrating the interaction of various feedback components of the cooling feedback system of FIG. 13 to control the cooling process of patient.

FIG. 14 is a flowchart illustrating the interaction of various feedback components to control the cooling of patient 12. Controller 246 may receive user input from a user (260). The user input received by controller 246 may include a programmed target core body temperature, a minimum skin temperature, high and low temperature ranges, a minimum heart rate, high and low oxygen saturation levels, high and low end-tidal carbon dioxide levels or the like.

Sensors within cooling device 244 or separate from the cooling garments generate signals as a function of a patient parameter (261). For instance, a sensor 54 within one of the cooling garments of cooling device 244 may generate a signal as a function of the temperature of patient 12. A communication link may relay the signal to a processor within cooling device 244 for processing. The processor may receive signals from multiple sensors, and may process the signals in order to generate a signal that represents the information from the multiple sensors. Communication bundles 245 may relay the raw or processed signals from cooling device 244 to controller 246 (262).

Controller 246 receives a signal via communication bundle 245 (264). For example, controller 246 may receive a signal indicating the core body temperature of patient 12 within headgear 228 and another signal indicating the core body temperature of patient 12 within body gear 230. Controller 246 compares the received signals with the input values received from the user (266), and determines whether the cooling device 244 is operating within an appropriate range (268). For example, controller 246 may receive the core body temperature of patient 12 within headgear 228, and compare the actual core body temperature of patient 12 with the target core body temperature input by the user.

When cooling device 244 is operating out of the appropriate operating range, e.g., below a target core body temperature, controller 246 may determine whether another variable has a higher priority (270). Controller 246 may be receiving a plurality of signals as a function of a plurality of patient parameters, and a parameter such as an abnormal heart rate or rhythm may have a higher priority in determining the operation of cooling device 244. When no other parameter has a higher priority, controller 246 may generate a regulation signal indicating to regulator 248 the adjustments necessary to bring cooling device 244 to the appropriate operating range or to maintain cooling device 244 in the appropriate operating range (272). Controller 246 may send the regulation signal to regulator 248 via feedback link 249 (274). Regulator 248 receives the signal from controller 246 (276), and regulates the delivery of coolant, carrier gas, and/or warm air according to the regulation signal (278). When the regulation signal indicates that cooling device 244 is operating in a range that may cause patient 12 to suffer frostbite, for example, regulator 248 may close a carrier gas supply valve, increase the temperature of the coolant, decrease the flow rate of coolant, adjust the mixing ratio of the coolant, or otherwise adjust the operation of cooling device 244. In this manner, controller 246 may include an algorithm for prevention of frostbite.

The invention may provide numerous advantages. The feedback system may provide for a safe yet rapid lowering of the temperature of the patient, by continuously monitoring the condition of the patient. Should the patient be at risk of frostbite, for example, the system may automatically perform adjustments to reduce that risk. In addition, the system may respond to conditions other than temperature, and may regulate therapy as a function of those conditions. The system may further alert a health care professional of life-threatening conditions, such as a serious arrhythmia or cardiac arrest.

In addition, the feedback system may regulate one or more cooling garments simultaneously. Each garment may be regulated individually for enhanced effect. Regulation of multiple garments allows the garments to work together in concert.

Furthermore, the feedback system is versatile and can be customized to the needs of each patient. A user may program the system to supply appropriate therapy for the patient.

The cooling garments and feedback system may further allow for hands free operation. For example, once on the body of the patient, the user may administer other treatments such as resuscitation. In addition, the cooling garments may be constructed to be light and portable in some embodiments, and may be brought to the patient at the site of the traumatic event, or at least may be contained in an ambulance.

Various embodiments of the invention have been described. For example, the cooling feedback system may include different cooling algorithms for different traumatic events. The cooling feedback system may include separate cooling algorithms for traumatic events in which the patient has no blood flow, e.g., cardiac arrest, as opposed to traumatic events in which the patient maintains blood flow, e.g., brain injury and stroke. For instance, when the patient suffers a traumatic event in which the patient has no blood flow, the blood does not circulate through the body and, in turn, cools faster. Therefore, an algorithm for traumatic events in which the patient has no blood flow may include a more conservative cooling therapy. These and other embodiments are within the scope of the following claims.

The invention claimed is:

1. A system comprising:
   a cooling garment for contacting a portion of the body of a patient, and having a coolant and a carrier gas for delivery to the body of the patient;
   a sensor within the cooling garment;
   a warm air supply for delivering warm air to the patient; and
   a controller for controlling the cooling garment in response to a signal from the sensor and controlling delivery of the warm air.

2. The system of claim 1, wherein the controller controls delivery of at least one of the carrier gas and the coolant.

3. The system of claim 2, wherein controlling the delivery comprises controlling one of a temperature, a pressure, and a flow rate.

4. The system of claim 1, wherein the carrier gas is a mixture of more than one gas, and wherein the controller controls a mixing ratio of the carrier gas.

5. The system of claim 1, wherein the coolant is a mixture of more than one liquid, and wherein the controller controls a mixing ratio of the coolant.

6. The system of claim 1, wherein the cooling garment further comprises:
   a spacer for separating at least part of the cooling garment from the body defining a space;
   a coolant delivery conduit for delivering the coolant to the body in the space;
   a carrier gas intake port in the cooling garment for fluidly connecting the space to a carrier gas supply; and
   an exit port in the cooling garment for fluidly connecting the space to an exterior environment.

7. The system of claim 6, wherein the coolant delivery conduit includes apertures from which the coolant exits the coolant delivery conduit.

8. The system of claim 6, further comprising a carrier gas mover for circulating the carrier gas within the space.

9. The system of claim 8, wherein the controller controls the speed at which the carrier gas mover circulates the carrier gas.

10. The system of claim 8, wherein the carrier gas mover includes one of a fan, a pressurized gas supply, and a pump.

11. The system of claim 1, wherein the controller further comprises a processor for receiving the signal.

12. The system of claim 11, further comprising a communication link that relays the signal from the sensor to the processor.

13. The system of claim 12, wherein the communication link is one of an optical fiber link, a wireless link, and a wire link.

14. The system of claim 1, wherein the sensor includes one of an oxygen sensor, a carbon dioxide sensor, a velocity Doppler probe, an electrocardiogram (ECG) sensor, and an electroencephalograph (EEG) sensor.

15. The system of claim 1, wherein the cooling garment includes a headgear for contacting at least a portion of the head.

16. The system of claim 15, wherein the headgear further includes an inner and outer shell.

17. The system of claim 1, wherein the cooling garment includes a body gear for contacting at least a portion of the body.

18. The system of claim 17, wherein the body gear includes at least one of an upper body gear and a lower body gear.

19. The system of claim 18, wherein the upper body gear is adapted to cover at least a portion of the armpit of the body.

20. The system of claim 18, wherein the lower body gear is adapted to cover at least a portion of the groin of the body.

21. The system of claim 1, wherein the garment includes:
a headgear for contacting at least a portion of the head; and
a body gear for contacting at least a portion of the body.

22. The system of claim 21, wherein the controller controls the headgear independently from the body gear.

23. The system of claim 1, wherein the cooling garment includes:
an inner shell configured to be proximate to a body part of the patient when in use, a space between the body part and the inner shell being an inner space;
an outer shell surrounding the inner shell, a space between the outer shell and the inner shell being an outer space in fluid communication with the inner space; and
an exit port for expelling the coolant in gaseous form and the carrier gas.

24. The system of claim 1, wherein the patient suffers from one of a brain injury, a stroke, and cardiac arrest.

25. A method comprising:
delivering a carrier gas and a coolant to a cooling garment in contact with the body of a patient;
generating a signal as a function of a patient parameter via a sensor within the cooling garment; and
controlling the cooling garment in response to the generated signal, wherein controlling the cooling garment includes:
operating the cooling garment to cool the patient at a first rate, and operating the cooling garment to cool the patient at a second rate in response to the generated signal, and wherein operating the cooling garment to cool the patient at a second rate in response to the generated signal includes operating the cooling garment to cool the patient at a second rate in response to a temperature of the patient falling below a frostbite temperature.

26. The method of claim 25, wherein the sensor is in contact with the body of the patient.

27. The method of claim 25, wherein the sensor is proximate to the body of the patient.

28. The method of claim 25, wherein the sensor includes one of a velocity Doppler probe, an electrocardiogram (ECG) sensor, and an electroencephalograph (EEG) sensor, an oxygen sensor, a carbon dioxide sensor, and a heart rate sensor.

29. The method of claim 25, further comprising relaying the signal to a processor via a communication link.

30. The method of claim 29, wherein the communication link relaying the signal is one of an optical fiber link, a wireless link, and a wire link.

31. The method of claim 30, wherein controlling the delivery comprises controlling one of a temperature, a pressure, a mixing ratio, and a flow rate.

32. The method of claim 29, further comprising controlling delivery of at least one of a coolant, a carrier gas, and a warm air supply.

33. The method of claim 25, wherein controlling the cooling apparatus further comprises:
receiving a signal from a communication link;
comparing the signal with a target value input by a user to determine whether the cooling garment is within an appropriate operating range; and
sending a regulation signal to a regulator when the cooling garment is not within the appropriate operating range.

34. The method of claim 25, wherein the cooling garment includes a headgear and a body gear, and controlling the cooling garment includes controlling the headgear and body gear individually.

35. The method of claim 25, wherein the patient parameter is one of oxygen saturation levels, blood flow, heart rate, brain electrical action, end tidal carbon dioxide levels.

36. A system comprising:
a coolant supply for supplying coolant to a cooling garment that contacts a portion of a body of a patient;
a carrier gas supply for supplying carrier gas to the cooling garment;
a warm air supply for supplying warm air to a body part of the patient when in use; and
a regulator for regulating at least one of the coolant supply, the carrier gas supply and the warm air supply as a function of a patient parameter.

37. The system of claim 36, wherein the patient parameter includes one of oxygen saturation levels, blood flow, heart rate, brain electrical action, end tidal carbon dioxide levels.

38. The system of claim 36, wherein the regulator regulates at least one of a temperature, a pressure, a mixing ratio, and a flow rate of at least one of the coolant supply, the carrier gas supply, and the warm air supply.

39. The system of claim 36, wherein the cooling garment includes a headgear and a body gear.

40. The system of claim 36, further comprising a controller for receiving a signal as a function of a patient parameter, and sends a regulation signal to the regulator.

* * * * *